United States Patent
Sato et al.

(10) Patent No.: US 8,426,376 B2
(45) Date of Patent: Apr. 23, 2013

(54) ANGIOGENESIS INHIBITOR

(75) Inventors: Yasufumi Sato, Sendai (JP); Hikaru Sonoda, Osaka (JP); Hideki Ohta, Osaka (JP)

(73) Assignee: Tohoku Technoarch Co., Ltd., Sendai-shi (JP)

( * ) Notice: Subject to any disclaimer, the term of this patent is extended or adjusted under 35 U.S.C. 154(b) by 555 days.

(21) Appl. No.: 12/702,272

(22) Filed: Feb. 8, 2010

(65) Prior Publication Data

US 2010/0256224 A1 Oct. 7, 2010

Related U.S. Application Data

(63) Continuation of application No. 11/722,799, filed as application No. PCT/JP2005/023304 on Dec. 20, 2005, now abandoned.

(30) Foreign Application Priority Data

Jan. 5, 2005 (JP) .................................. 2005-000476

(51) Int. Cl.
*A61K 31/7088* (2006.01)
*C12Q 1/68* (2006.01)
*A61P 9/10* (2006.01)

(52) U.S. Cl.
USPC .............................................. 514/44 R; 435/6

(58) Field of Classification Search .................... None
See application file for complete search history.

(56) References Cited

U.S. PATENT DOCUMENTS

| 2004/0102613 | A1 | 5/2004 | Horiguchi et al. | |
|---|---|---|---|---|
| 2005/0158719 | A1* | 7/2005 | Sato et al. .................. | 435/6 |
| 2005/0176632 | A1 | 8/2005 | Ohtaki et al. | |
| 2007/0148676 | A1 | 6/2007 | Kachalsky et al. | |

FOREIGN PATENT DOCUMENTS

| EP | 1074617 A2 | 2/2001 |
|---|---|---|
| JP | 2003-144177 A | 5/2003 |
| WO | WO02/090546 | * 11/2001 |
| WO | WO 02/074961 | 9/2002 |
| WO | WO 02/090546 | 11/2002 |

OTHER PUBLICATIONS

Maisonpierre, P. C., et al., "Angiopoietin-2, a Natural Antagonist for Tie2 That Disrupts in vivo Angiogenesis," Science, vol. 277, pp. 55-60 (1997).
Carmeliet et al., "Angiogenesis in cancer and other diseases", *Nature*, vol. 407 (2000), pp. 249-257.
Kerbel, "Vasohibin: the feedback on a new inhibitor of angiogenesis", *Journal of Clinical Investigation*, vol. 114, No. 7 (2004), pp. 884-886.
Shimizu et al., "Gene Regulation of a Novel Angiogenesis Inhibitor, vasohibin, in endothelial cells", *Biochemical and Biophysical Research Communications*, vol. 327 (2005), pp. 700-706.
Tateishi-Yuyama et al., "Therapeutic angiogenesis for patients with limb ischaemia by autologous transplantation of bone-marrow cells: a pilot study and a randomized controlled trial", *Lancet*, vol. 360 (2002), pp. 427-435.
Watanabe et al., "Vasohibin as an endothelium-derived negative feedback regulator of angiogenesis", *Journal of Clinical Investigation*, vol. 114, No. 7, (2004), pp. 898-907.
Shibuya, T., et al. Arterioscler. Thromb. Vasc. Biol. 27:1051-1057, 2006.
Kimura, H., et al. Blood, 113: 4810-4818, 2009.
Bowie, et al. (Science, 247: 1306-1319, 1990).
Burgess, et al. (J. Cell Biology, 111: 2129-2138, 1990).
Lazar, et al. (Molecular and Cellular Biology, 8: 1247-1252, 1988).
International Preliminary report on Patentability (Jul. 19, 2007).

* cited by examiner

*Primary Examiner* — Scott Long
(74) *Attorney, Agent, or Firm* — Birch, Stewart, Kolasch & Birch, LLP

(57) ABSTRACT

Because AK022567 has angiogenesis inhibitory activity, it is useful as an angiogenesis inhibitor. Furthermore, 4 splicing variants obtained from the same gene are also useful as an angiogenesis inhibitor. These 5 polypeptides, polynucleotides encoding the polypeptides and antibodies against the polypeptides are useful for screening of a candidate compound as an angiogenesis inhibitor or promoter. A compound obtained from the screening is useful as a medicine and can be used for a preventive or therapeutic agent for an angiogenesis related disease.

2 Claims, 4 Drawing Sheets

Figure 2

```
VhRP         1                                   MTGSAADTH RCPHPKGAKG TRSRSSHARP VSLATSGGSE EEDKDGGVLF
                                                 .*...... .*........ .......... .*..*....* .****.*
Vasohibin    1"  MPGGKKVAGG GSSGATPTSA AATAPSGVRR LETSEGTSAQ                                  EDLRDGGVPF 50'  HVNKSGFPID SHTWERMWMH VAKVHPKGGE MVGAIRNAAF LAKPSIPQVP                       NYRLSMTIPD
                 **..*...** .*.******* .*.****. ...... ..**.*.*
            61"  FVNRGGLPVD EATWERMWKH VAKIHPDGEK VAQRIRGATD LPKIPIPSVP                       TFQPSTPVPE 110'  WLQAIQNYMK TLQYNHTGTQ FFEIRKMRPL SGLMETAKEM TRESLPIKCL                       EAVILGIYLT
                 .*.*.*.*.* .******* ***.*. .*.**. *.***.                       ******
           121"  RLEAVQRYIR ELQYNHTGTQ FFEIKKSRPL TGLMDLAKEM TKEALPIKCL                       EAVILGIYLT 170'  MGQPSTEREFP ISFKTYFSGN YFHMWLGIY CNGRYGSLGM SRRAEFLMDKP                      LTFRTLSDLI
                 *..*.**** ***** ..*.*.. ..***. *..
           181"  NSMPTLEREFP ISFKTYFSGN YFRHIVLGVN FAGRYGALGM SRREDLMYKP                       PAFRTLSELV 230'  EDEEDSYKKY LHTVKKVKIG LYVPHEPHSF QPIEWKQLVL NVSKMLRADI                       RKELEKYARD
                 .***.*.. ...**.*. .....* ..****.*.* *..***.*.*                       ***.**
           241"  LDEEAAYGRC WHVLKKVKLG QSVSHDPHSV EQIEWKHSVL DVERLGRDDF                       RKELERHARD 290'  MRMKILKPAS AHSPTQVRSR GKSLSPRRRQ ASPPRRLGRR EKSPALPEKK                       VADLSTLNEV
                 ..*..* ..***.*..  *.****.  .*.***.*.*
           301"  MRLKIGKGTG PPSPTKDRKK DVS-SPQRAQ SSPHRRNSRS ERRPS-GDKK                       TSEPKAMPDL

350'  -GYQIRI
                 *****.
           359"  NGYQIRV
```

ANGIOGENESIS INHIBITOR

This application is the Continuation of U.S. application Ser. No. 11/722,799 filed Jan. 18, 2008, which is the U.S. National Stage of International Application No. PCT/JP2005/023304, filed Dec. 20, 2005, which claims priority under 35 USC §119 to Japanese Patent Application No. 2005-000476, filed Jan. 5, 2005.

FIELD OF THE INVENTION

This invention relates to an angiogenesis inhibitor or promoter. Additionally, this invention relates to a method for screening an angiogenesis inhibitor or promoter and a kit for the method.

BACKGROUND ART

Angiogenesis means a phenomenon that a new vessel is formed from a pre-existing venula or capillary vessel in an animal tissue or organ by migration, growth and lumen formation of a vascular endothelial cell. In general, new vessels are formed and elongated during the fetal period, childhood or growth period. However, after the growth period, a stage that angiogenesis occurs in a body is limited. Angiogenesis occurs under the usual physical condition such as luteinization, ovulate, embryogenesis, placenta formation or the like, furthermore, under wound healing or inflammation restoration. As above, angiogenesis occurs under the healthy condition and plays an important role for tissue restoration. Additionally, it has become clear that promotion of angiogenesis is effective on therapy of a coronary heart disease such as myocardial infarction, arteriosclerosis obliterans or a peripheral vascular disease such as Buerger's disease. It has also been reported that angiogenesis was induced by transplant of marrow cells to perform therapy of arteriosclerosis (Non-patent Document 1). Induction of angiogenesis is important for prevention and therapy of the above diseases.

It is also known that capillary vessels are increased and cause serious damage of a tissue in a lot of chronic diseases such as diabetes. When malignant tumor grows, a tumor cell directly induces angiogenesis by an angiogenesis promoter to obtain nutrition or oxygen which is necessary for growth of the tumor cell. The tumor cell grows more by obtaining nutrition through a new vessel. Metastasis to other organ or part induces angiogenesis and a tumor cell moves with blood flow. As a disease that angiogenesis causes the disease or relates to get worse the state of the disease, vascular disease, inflammatory disease, entoptic neovascular disease, reproductive system disease, central nervous system disease, cancer or the like has been reported (Non-patent Document 2). Inhibition of angiogenesis is important for prevention and therapy of the above diseases.

AK022567 (SEQ ID: 1), BC051856 (SEQ ID: 3), BC053836 (SEQ ID: 5) and BC028194 (SEQ ID: 7) are disclosed on Database of GenBank with proteins which the genes encode. However, the relation of these genes and angiogenesis has not been reported.

[Non-patent Document1] Tateishi-Yuyama, E., et al., The LANCET, Vol. 360, pp. 427-435 (2002)

[Non-patent Document 2] Carmeliet, P., et al., Nature, Vol. 407, pp. 249-257 (2000)

DISCLOSURE OF THE INVENTION

Problems to be Solved by the Invention

This invention provides an angiogenesis inhibitor or promoter relating to a novel angiogenesis inhibiting factor. Additionally, it provides a method for efficiently screening a angiogenesis inhibitor or promoter with a novel angiogenesis inhibiting factor or a kit for easily and quickly screening by the above method for screening.

Means for Solving the Problem

The inventors have intensively studied and found that AK022567 protein is a novel angiogenesis inhibiting factor. Additionally, they found that 3 splicing variants obtained from the same gene encoding AK022567 protein, BC051856 protein (SEQ ID: 4), BC053836 protein (SEQ ID: 6) and BC028194 protein (SEQ ID: 8), have angiogenesis inhibitory activity. Furthermore, they found a novel splicing variant (SEQ ID: 10). They found that the above 5 proteins, polynucleotides encoding the proteins, neutralizing antibodies against them or the like can be used as an angiogenesis inhibitor or promoter to accomplish this invention.

AK022567 protein (SEQ ID: 2) has homology of 58% with Vasohibin protein (SEQ ID: 12, WO02/090546) which is known as an angiogenesis inhibitor.

AK022567 protein and Vasohibin protein have the following differences.

AK022567 proteins were not found to express in vascular endothelial cells, while Vasohibin proteins were found to express in them. AK022567 proteins were found to express in human fetus but not in a tissue of human adult such as brain or placenta, while Vasohibin proteins were found to express in human fetus and brain or placenta of human adult.

This invention is (1) an angiogenesis inhibitor comprising
a protein having an amino acid sequence selected from the group consisting of SEQ ID NO: 2, 4, 6, 8 and 10,
a protein having the amino acid sequence with deletion, substitution or addition of one or several amino acid residue(s) and angiogenesis inhibitory activity,
a partial peptide thereof having angiogenesis inhibitory activity
or a salt thereof, (2) an expression vector for inhibiting angiogenesis, comprising
a polynucleotide which encodes a protein having an amino acid sequence selected from the group consisting of SEQ ID NO: 2, 4, 6, 8 and 10, a protein having the amino acid sequence with deletion, substitution or addition of one or several amino acid residue(s) and angiogenesis inhibitory activity or a partial peptide thereof having angiogenesis inhibitory activity,
or a polynucleotide fragment thereof having angiogenesis inhibitory activity, (3) an expression vector for inhibiting angiogenesis, comprising a polynucleotide hybridizing under a stringent condition with a polynucleotide encoding a protein having an amino acid sequence selected from the group consisting of SEQ ID NO: 2, 4, 6, 8 and 10, a protein having the amino acid sequence with deletion, substitution or addition of one or several amino acid residue(s) and angiogenesis inhibitory activity or a partial peptide thereof having angiogenesis inhibitory activity, and encoding a protein having angiogenesis inhibitory activity,
or a polynucleotide fragment thereof having angiogenesis inhibitory activity, (4) an angiogenesis promoter comprising a neutralizing antibody against a protein having an amino acid sequence selected from the group consisting of SEQ ID NO: 2, 4, 6, 8 and 10, a protein having the amino acid sequence with deletion, substitution or addition of one or several amino acid residue(s) and angiogenesis inhibitory activity, a partial peptide thereof having angiogenesis inhibitory activity or a salt thereof, (5) a method for screening an angiogenesis inhibitor, characterized by selecting a compound or a salt thereof, wherein the compound promotes angiogenesis inhibitory activity of a protein having an amino acid sequence selected from the group consisting of SEQ ID NO: 2, 4, 6, 8 and 10, a protein having the amino acid sequence with deletion, substitution or addition of one or several amino acid residue(s) and angiogenesis inhibitory activity, a partial peptide thereof having angiogenesis inhibitory activity or a salt thereof, (6) a method for screening an angiogenesis inhibitor, characterized by selecting a compound or a salt thereof, wherein the compound promotes gene expression of a protein having an amino acid sequence selected from the group consisting of SEQ ID NO: 2, 4, 6, 8 and 10, a protein having the amino acid sequence with deletion, substitution or addition of one or several amino acid residue(s) and angiogenesis inhibitory activity or a partial peptide thereof having angiogenesis inhibitory activity, (7) a method for screening an angiogenesis promoter, characterized by selecting a compound or a salt thereof, wherein the compound inhibits angiogenesis inhibitory activity of a protein having an amino acid sequence selected from the group consisting of SEQ ID NO: 2, 4, 6, 8 and 10, a protein having the amino acid sequence with deletion, substitution or addition of one or several amino acid residue(s) and angiogenesis inhibitory activity, a partial peptide thereof having angiogenesis inhibitory activity or a salt thereof, (8) a method for screening an angiogenesis promoter, characterized by selecting a compound or a salt thereof, wherein the compound inhibits gene expression of a protein having an amino acid sequence selected from the group consisting of SEQ ID NO: 2, 4, 6, 8 and 10, a protein having the amino acid sequence with deletion, substitution or addition of one or several amino acid residue(s) and angiogenesis inhibitory activity or a partial peptide thereof having angiogenesis inhibitory activity, (9) a kit for the method for screening of any one of (5)-(8), comprising a protein having an amino acid sequence selected from the group consisting of SEQ ID NO: 2, 4, 6, 8 and 10, a protein having the amino acid sequence with deletion, substitution or addition of one or several amino acid residue(s) and angiogenesis inhibitory activity, a partial peptide thereof having angiogenesis inhibitory activity or a salt thereof,

(10) a kit for the method for screening of any one of (5)-(8), comprising a polynucleotide which encodes a protein having an amino acid sequence selected from the group consisting of SEQ ID NO: 2, 4, 6, 8 and 10, a protein having the amino acid sequence with deletion, substitution or addition of one or several amino acid residue(s) and angiogenesis inhibitory activity or a partial peptide thereof having angiogenesis inhibitory activity, or a polynucleotide fragment thereof having angiogenesis inhibitory activity,

(11) a method for inhibiting angiogenesis characterized by using an angiogenesis inhibitor described in (1) or (4) or an expression vector for inhibiting angiogenesis described in (2) or (3),

(12) a method for treating angiogenesis, vascular disease, inflammatory disease, entoptic neovascular disease, reproductive system disease, central nervous system disease or malignant neoplasma characterized by giving an angiogenesis inhibitor described in (1) or (4) or an expression vector for inhibiting angiogenesis described in (2) or (3),

(13) use of a protein having an amino acid sequence selected from the group consisting of SEQ ID NO: 2, 4, 6, 8 and 10, a protein having the amino acid sequence with deletion, substitution or addition of one or several amino acid residue(s) and angiogenesis inhibitory activity, a partial peptide thereof having angiogenesis inhibitory activity or the salt thereof for producing a preventive or therapeutic agent for angiogenesis, vascular disease, inflammatory disease, entoptic neovascular disease, reproductive system disease, central nervous system disease or malignant neoplasma, and

(14) use of a polynucleotide which encodes a protein having an amino acid sequence selected from the group consisting of SEQ ID NO: 2, 4, 6, 8 and 10, a protein having the amino acid sequence with deletion, substitution or addition of one or several amino acid residue(s) and angiogenesis inhibitory activity or a partial peptide thereof having angiogenesis inhibitory activity for producing a preventive or therapeutic agent for angiogenesis, vascular disease, inflammatory disease, entoptic neovascular disease, reproductive system disease, central nervous system disease or malignant neoplasma.

Effect Of The Invention

A protein having an amino acid sequence selected from the group consisting of SEQ ID NO: 2, 4, 6, 8 and 10 has angiogenesis inhibitory activity. Therefore, the protein, a polynucleotide encoding the protein or the like can be used as an angiogenesis inhibitor. A neutralizing antibody against the protein or polynucleotide can be used as an angiogenesis promoter. Furthermore, an angiogenesis inhibitor or promoter can be screened with the protein, polynucleotide, neutralizing antibody or the like. A compound obtained in the screening process can be safely used as a preventive or therapeutic agent for an angiogenesis related disease.

BRIEF DESCRIPTION OF THE DRAWINGS

FIG. 1 5 variants of a gene encoding a protein of this invention.

FIG. 2 Amino acid homology of Variant 5 (SEQ ID NO: 10) and Vasohibin (SEQ ID NO: 12).

BEST MODE FOR CARRYING OUT THE INVENTION

Figure 1:
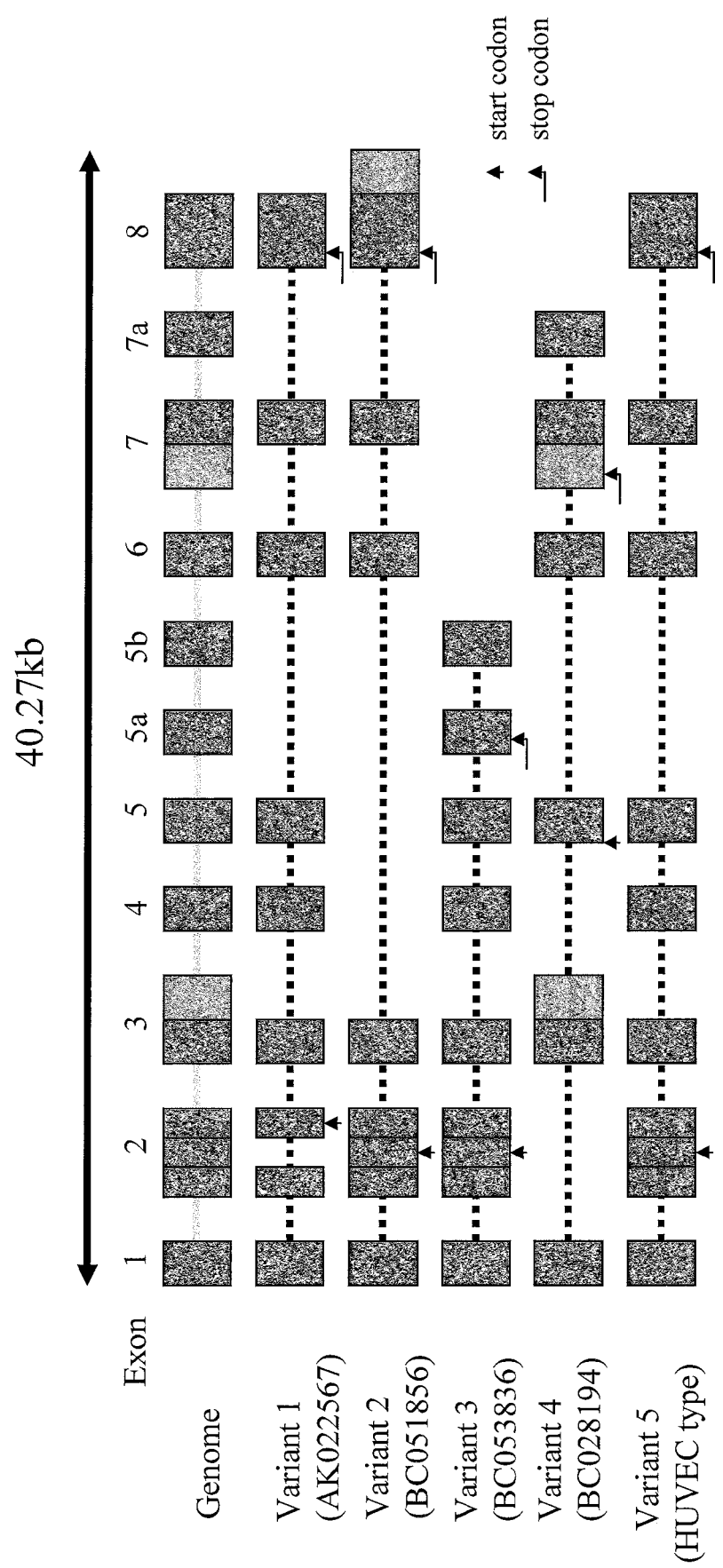

Terms used in this description have the usual meanings in this field except for the case especially mentioned. Terms especially used in this description are explained below.

"Angiogenesis" means a phenomenon that a vascular endothelial cell germinates from a pre-existing vessel and a capillary vessel is formed in a way that goes into a tissue. Formative process is 1) digestion of vascular basement membrane by a protease, 2) migration/growth of a vascular endothelial cell, and then 3) lumen formation.

"Angiogenesis related disease" is vascular disease such as arterial sclerosis, hypertonia, angina pectoris, obstructive arteriosclerosis, myocardial infarction, cerebral infarction, diabetic angiopathy or vascular malformation; inflammatory disease such as hepatitis, pneumonitis, glomerular nephritis, thyreoiditis, osteitis, arthromeningitis, osteoclasia, chondrolysis, rheumatism, bronchial asthma, sarcoidosis, Crow-Fukase syndrome, pannus, allergic oedema, ulcers, hydroperitoneum, peritoneal screlosis or tissular conglutination; entoptic neovascular disease such as diabetic retinopathy, occlusion of retinal vein or aging macular degeneration; reproductive system disease such as uterus dysfunction, placental dysfunction, ovarian hyperergasia or follicle cyst; central nervous system disease such as retinosis, cerebral apoplexy, vascular dementia or Alzheimer disease; cancer such as solid cancer, angiomatous, hemangioendothelioma, sarcomas, Kaposi's sarcoma or hematopoietic organic ulcer.

"An angiogenesis inhibitor" has angiogenesis inhibitory activity by using or promoting activity of a protein having novel angiogenesis inhibitory activity and an amino acid sequence selected from the group consisting of SEQ ID NO: 2, 4, 6, 8 and 10. It is, for example, a protein having an amino acid sequence selected from the group consisting of SEQ ID NO: 2, 4, 6, 8 and 10, a substance comprising a polynucleotide encoding the protein or the like, a substance comprising a compound which is obtained by a method for screening with the protein or the like and has promoting activity of angiogenesis inhibitory activity of the protein, the salt or the like. The angiogenesis inhibitor can be used as a preventive or therapeutic agent for a disease whose condition can become serious by angiogenesis in the above diseases. The disease on which the angiogenesis inhibitor has effect is vascular disease, inflammatory disease, entoptic neovascular disease, reproductive system disease, central nervous system disease, cancer or the like.

"An angiogenesis promoter" has angiogenesis inducing activity by inhibiting activity of a protein having novel angiogenesis inhibitory activity and an amino acid sequence selected from the group consisting of SEQ ID NO: 2, 4, 6, 8 and 10. It is, for example, a substance comprising a neutralizing antibody recognizing the protein, a polynucleotide encoding the protein or the like, a substance comprising a compound which is obtained by a method for screening with the protein or the like and has inhibitory activity of angiogenesis inhibitory activity of the protein, the salt or the like. The angiogenesis promoter can be used as a preventive or therapeutic agent for a disease whose condition can become lighter by angiogenesis in the above diseases. The disease on which the angiogenesis promoter has effect is wound healing, restoration of inflammation, coronary heart disease, peripheral vascular disease, arteriosclerosis or the like.

"A protein having an amino acid sequence selected from the group consisting of SEQ ID NO: 2, 4, 6, 8 and 10" (hereinafter referred to as "a protein of this invention") can be a protein obtained from a cell of human or a homoiothermic animal (e.g., guinea pig, rat, mouse, chicken, rabbit, pig, sheep, cattle or monkey) (e.g., hepatic cell, splenocyte, nerve cell, gliocyte, pancreatic (βcell, marrow cell, mesangial cell, Langerhans cell, epidermal cell, epithelial cell, caliciform cell, endothelial cell, smooth muscle cell, fibroblast, fibrocyte, muscular cell, adipocyte, immunocyte (e.g., macrophage, T cell, B cell, natural killer cell, mastocyte, neutrophilic leukocyte, basocyte, acidocyte or monocyte), megakaryocyte, synovial cell, chondrocyte, osteocyte, osteoblast, osteoclast, alveolar epithelial cell, hepatic cell, intersitial cell, a precursor cell thereof, a stem cell, carcinoma cell or the like) or any tissue in which the above cells exist, for example, brain, each part of brain (e.g., olfactory bulb, amygdaloid nucleus, basal ganglia, hippocampus, thalamus, hypothalamus, cerebral cortex, medulla oblongata or cerebellum), spinal cord, pituitary gland, stomach, pancreas, kidney, liver, genital gland, thyroid gland, gallbladder, bone marrow, adrenal gland, skin, muscle, lung, digestive canal (e.g., large intestine or small intestine), blood vessel, heart, thymus gland, spleen, submaxillary gland, peripheral blood, prostate gland, testes, ovary, placenta, uterus, bone, arthrosis, skeletal muscle or the like.

"An amino acid sequence with deletion, substitution or addition of one or several amino acid residue(s)" means, for example, (A) an amino acid sequence selected from the group consisting of SEQ ID NO: 2, 4, 6, 8 and 10 with deletion of 1, 2 or more amino acid residue(s) (preferably about 1-30, more preferably about 1-10, much more preferably several (1-5) amino acid residue(s)), (B) an amino acid sequence selected from the group consisting of SEQ ID NO: 2, 4, 6, 8 and 10 with substitution of 1, 2 or more amino acid residue(s) (preferably about 1-30, more preferably about 1-10, much more preferably several (1-5) amino acid residue(s)), (C) an amino acid sequence selected from the group consisting of SEQ ID NO: 2, 4, 6, 8 and 10 with addition of 1, 2 or more amino acid residue(s) (preferably about 1-30, more preferably about 1-10, much more preferably several (1-5) amino acid residue(s)), or (D) an amino acid sequence which the above amino acid sequences are combined. When the amino acid sequence has deletion, substitution or addition, the position of the deletion, substitution or addition is not especially restricted. However, a protein used in this invention with deletion, substitution or addition should be a polypeptide having angiogenesis inhibitory activity. It is, for example, a polypeptide having homology of at least 60% or more, preferably 80% or more and more preferably 95% or more with an amino acid sequence selected from the group consisting of SEQ ID NO: 2, 4, 6, 8 and 10.

"A partial peptide of a protein" is any partial peptide of the above protein of this invention, preferably having the same character as the protein of this invention. For example, it is a peptide having an amino acid sequence consisting of at least 20 or more, preferably 50 or more, more preferably 70 or more, much more preferably 100 or more, most preferably 200 or more residues of a complete amino acid sequence of a protein of this invention or the like.

Additionally, "a partial peptide" can have deletion of 1, 2 or more amino acid residue(s) (preferably about 1-10, more preferably several (1-5) amino acid residue(s)) in the amino acid sequence, substitution of 1, 2 or more amino acid residue(s) (preferably about 1-20, more preferably about 1-10, much more preferably several (1-5) amino acid residue(s)) in the amino acid sequence or addition of 1, 2 or more amino acid residue(s) (preferably about 1-20, more preferably about 1-10, much more preferably several (1-5) amino acid residue(s)) in the amino acid sequence, if it has angiogenesis inhibitory activity. It is, for example, a polypeptide having homology of at least 60% or more, preferably 80% or more and more preferably 95% or more with an amino acid sequence selected from the group consisting of SEQ ID NO: 2, 4, 6, 8 and 10.

"A salt of a protein or the partial peptide" is a salt of physiologically acceptable acid (e.g., mineral acid, organic acid), base (e.g., alkali metal salt) or the like and physiologically acceptable acid addition salt is especially preferable. It is, for example, a salt of mineral acid (e.g., hydrochloric acid, phosphoric acid, hydrobromic acid or sulfuric acid), organic acid (e.g., acetic acid, formic acid, proprionic acid, fumaric acid, Maleic acid, succinic acid, tartaric acid, citric acid, malic acid, oxalic acid, benzoic acid, methanesulfonic acid or benzenesulfonic acid) or the like.

"A polynucleotide hybridizing under a stringent condition" means a polynucleotide obtained by a generally known and common method in this field with a fragment of a polynucleotide encoding a protein of this invention as a probe, for example, colony hybridization, plaque hybridization or Southern blotting hybridization. To be more precise, it includes a polynucleotide identified by hybridizing at 65° C. in the presence of 0.7 to 1.0M NaCl with a membrane immobilized polynucleotides from colony or plaque and washing of the membrane at 65° C. with SSC (Saline Sodium Citrate; 150 mM sodium chloride, 15 mM sodium citrate) solution whose concentration is 0.1-fold to twice. Hybridization can be performed according to a method described in Molecular Cloning: Laboratory Manual, Second Edition (1989) (Cold Spring Harbor Laboratory Press), Current Protocols in Molecular Biology (1994) (Wiley-Interscience), DNA Cloning 1: Core Techniques, A practical Approach, Secon Edition (1995) (Oxford University Press) or the like. Preferably, sequences comprising of only adenine (A) or thymine (T) are excluded from sequences hybridizing under a stringent condition. "A fragment of a polynucleotide" includes a polynucleotide having serial base sequences in a base sequence of SEQ ID: 1, 3, 5, 7 or 9, for example, a polynucleotide having a base sequence of 5, 8, 10, 12, 15, 20, 25, 30, 50, 100, 500, 1000 bases or the like.

In this description, "a polynucleotide hybridizing" includes a polynucleotide hybridizing to the other polynucleotide under the above hybridizing condition. Examples of the above polynucleotide include a polynucleotide having a homology of at least 60% or more, preferably 80% or more and more preferably 95% or more with a base sequence of DNA encoding a protein of this invention. The homology is shown as a score, for example, by a search program BLAST with algorithm developed by Altschul et al (The Journal of Molecular Biology, 215, 403-410 (1990).).

"An antibody" means a general antibody in this field and includes a whole antibody, a fragment thereof, a derivative, a conjugation, a modified antibody or the like. Preferred is an antibody recognizing a protein of this invention or the partial protein. More preferred is an antibody recognizing specifically the protein. Much more preferred is an antibody recognizing monospecifically the protein. Furthermore, a neutralizing antibody inhibiting angiogenesis inhibitory activity of a protein of this invention is preferable. The antibody can be a polyclonal antibody or a monoclonal antibody. The antibody or the fragment can be labeled with a well-known enzyme (e.g., peroxidase), fluorescent dye, radioactive substance, avidin, biotin or the like.

A method for obtaining a polynucleotide encoding a protein of this invention (hereinafter referred to "a gene of this invention"), a method for producing the protein, a method for producing a neutralizing antibody against the protein or the like is described in detail below.

(1) A Method for Obtaining a Gene of this Invention cDNA library is manufactured from human brain, heart, skeletal muscle, spleen, kidney, liver, small intestine, placenta, a human normal cell from these tissues or a human umbilical vein endothelial cell by a usual method to obtain a gene of this invention. Especially preferred is to obtain the gene from human placenta or a human umbilical vein endothelial cell.

A method for manufacturing cDNA library is a method described in Molecular Cloning: A Laboratory Manual, Second Edition (1989) (Cold Spring Harbor Laboratory Press), Current Protocols in Molecular Biology (1994) (Wiley-Interscience), DNA Cloning 1: Core Techniques, A Practical Approach, Second Edition (1995) (Oxford University Press) or the like, or a method with a kit on the market, for example, Superscript Plasmid System for cDNA Synthesis and Plasmid Cloning (Invitrogen) or ZAP-cDNA Synthesis Kits (STRATAGENE).

cDNA obtained by the above method is, for example, DNA encoding a protein having an amino acid sequence from selected the group consisting of SEQ ID NO: 2, 4, 6, 8 and 10. To be more precise, it is DNA having a base sequence selected from the group of SEQ ID NO: 1, 3, 5, 7 and 9, or the like. The cDNA can be used for producing an expression plasmid which a gene of this invention is inserted in an appropriate expression vector. A method for using the expression vector, plasmid or the like is described in after-mentioned "a method for producing a protein of this invention". The above expression plasmid is, for example, a plasmid described in after-mentioned Example 2.

Additionally, DNA can be prepared by chemical synthesis of DNA encoding a protein of this invention based on an amino acid sequence. Chemical synthesis of DNA is performed with DNA synthesizer made by Shimadzu Corporation which uses a thiophosphate method, DNA synthesizer model 392 made by PerkinElmer, Inc. which uses a phosphoramidite method, or the like.

Furthermore, DNA can be prepared by PCR with a sense primer (SEQ ID: 13), an antisense primer (SEQ ID: 14) and cDNA obtained from mRNA in a cell, in which complementary mRNA to the primers expresses, as a template.

(2) A Method for Producing a Protein of this Invention

A protein of this invention can be produced by a method described in Molecular Cloning: A Laboratory Manual, Second Edition (1989) (Cold Spring Harbor Laboratory Press) or Current Protocols in Molecular Biology (1994) (Wiley-InterScience). For example, it can be produced by expressing a gene of this invention in a host cell by the following method.

DNA fragment of appropriate length comprising a part encoding the protein is prepared based on full-length DNA encoding a protein of this invention. DNA with substitutions is prepared as a base sequence encoding the protein has most appropriate codons for expression in a host. The DNA is useful to improve production rate of the protein. A recombinant DNA (an expression plasmid) is produced by inserting the DNA fragment or full-length DNA in a downstream of a promoter of an appropriate expression vector. A transformant producing a protein of this invention can be obtained by introducing the expression plasmid in a host cell which is appropriate for the expression vector.

Any cell in which a target gene can be expressed can be used as a host cell. The cell is a prokaryotic cell, yeast, an animal cell, a plant cell, an insect cell or the like. As an expression vector, a vector which can autonomously replicate in the above host cell or can be inserted into a chromosome and which includes a promoter at an appreciate position for transcription of a gene of a protein of this invention can be used.

(i) A case that a Prokaryote is Used as a Host.

An expression vector of a protein of this invention can autonomously replicate in a prokaryote and is preferably constructed with a promoter, a ribosome binding sequence, a gene of this invention and a transcription termination sequence. A gene regulating a promoter can be included in the vector.

An expression vector is, for example, pBTrp2, pBTac 1, pBTac2 (Roche Diagnostics), BluescriptII SK(+), BluescriptII SK(−) (STRATAGENE), pSTV28, pUC118, pUC19 (TaKaRa), pKK233-2 (Amersham Biosciences), pSE280, pSupex, pUB110, pTP5, pC194, pTrxFus (Invitrogen), pGEMEX-1 (Promega), pQE-8 (QIAGEN), pGEX (Pharmacia), pETsystem (Novagen), pMAL-c2 (New England BioLabs), pKYP10 (JP1982-110600), pKYP200 (Agricultural Biological Chemistry, 48, 669 (1984).), pLSA1 (Agricultural Biological Chemistry, 53, 277 (1989).), pGEL1 (Proceedings of the National Academy of Sciences USA, 82, 4306 (1985).), pEG400 (Journal of Bacteriology, 172, 2392 (1990).), pTrs30 (FERM BP-5407), pTrs32 (FERM BP-5408), pGHA2 (FERM BP-400), pGKA2 (FERM BP-6798), pPA1 (JP1987-233798) or pTerm2 (JP1990-22979, U.S. Pat. No. 4,686,191, U.S. Pat. No. 4,939,094, U.S. Pat. No. 5,160,735).

Any promoter which can express in a host cell such as *Escherichia coli* can be used. For example, it is a promoter from *Escherichia coli* or a phage such as trp promoter (Ptrp), lac promoter (Plac), PL promoter, PR promoter or PSE promoter; SPO1 promoter, SPO2 promoter, penP promoter or the like. An artificially modified promoter such as a promoter which two Ptrps is connected in series (Ptrp×2), tac promoter, lacT7 promoter or letI promoter can be used.

Preferred is a plasmid that a distance between Shine-Dalgarno sequence which is a ribosome binding sequence and an initiation codon is regulated to an appropriate distance, for example, 6 to 18 bases. A transcription termination sequence is not always needed for an expression of a gene of this invention, but it is preferably positioned at the right downstream of a structural gene.

A host cell is, for example, a prokaryote of *Escherichia* genus, *Serratia* genus, *Bacillus* genus, *Brevibacterium* genus, *Corynebacterium* genus, *Microbacterium* genus *Pseudomonas* genus or the like. Examples are XL1-Blue strain, XL2-Blue strain, DH1 strain, MC1000 strain, KY3276 strain, W1485 strain, JM109 strain, HB101 strain, No. 49 strain, W3110 strain, NY49 strain, BL21 (DE3) strain, BL21 (DE3) pLysS strain, HMS174 (DE3) strain and HMS174 (DE3) pLysS strain of *E. coli* as *Escherichia* genus; *S. ficaria* strain, *S. fonticola* strain, *S. liquefaciens* strain and *S. marcescens* strain as *Serratia* genus; *B. subtilis* strain and *B. amyloliquefaciens* strain as *Bacillus* genus; *B. ammoniagenes* strain, *B. Immariophilum* (ATCC:14068) strain and *B. saccharolyticum* (ATCC:14066) strain as *Brevibacterium* genus; *C. glutamicum* (ATCC:13032) strain, *C. glutamicum* (ATCC:14067) strain, *C. glutamicum* (ATCC:13869) strain and *C. acetoacidophilum* (ATCC:13870) strain as *Corynebacterium* genus; *M. ammoniaphilum* (ATCC:15354) strain as *Microbacterium* genus and *S. mephitica* strain as *Pseudomonas* genus.

Any method for introducing DNA to the above host cell can be used as a method for introducing an expression vector. For example, it is an electroporation (Nucleic Acids Research, 16, 6127 (1988).), calcium phosphate method (Proceedings of the National Academy of Sciences USA, 69, 2110 (1972).), protoplast method (JP1987-2483942) or a method described in Gene, 17, 107 (1982) or Molecular & General Genetics, 168, 111 (1979).

(ii) A Case that Yeast is Used as a Host

When yeast is used as a host, an expression vector is, for example, YEp13 (ATCC: 37115), YEp24 (ATCC: 37051), YCp50 (ATCC: 37419), pHS19 or pHS15.

Any promoter which express in yeast can be used as a promoter. For example, it is ADH1 (alcohol dehydrogenase) promoter, PHO5 (acid phosphatase) promoter, PGK1 (phosphoglycerate kinase) promoter, GAPDH (glyceraldehyde3-phosphate dehydrogenase) promoter, GALL (galactose kinase) promoter, GAL10 (UDP galactose4-epimerase) promoter, MFα1 (α pheromone) promoter or CUP1 (metallothionein) promoter.

A host is, for example, *S. cerevisiae* species of *Saccharomyces* genus, *S. pombe* species of *Schizosaccharomyces* genus, *K. lactis* species of *Kluyveromyces* genus, *T. pullulans* species of *Trichosporon* genus, *S. alluvius* species of *Schwanniomyces* genus or *P. pastoris* species of *Pichia* genus.

Any method for introducing DNA into a host can be used as a method for introducing an expression vector. For example, it is an electroporation (Methods in Enzymology, 194, 182 (1990)), a spheroplast method (Proceedings of the National Academy of Sciences USA, 84, 1929 (1978)) or a lithium acetate method (Journal of Bacteriology, 153, 163 (1983). or Proceedings of the National Academy of Sciences USA, 75, 1929 (1978)).

(iii) A Case that an Animal Cell is Used as a Host

When an animal cell is used as a host, an expression vector is, for example, pcDNA1/Amp, pcDNA1, pCDM8, pREP4 (Invitrogen), pHM6 (Roche Diagnostics), pKK223-3, pGEX (Amersham Biosciences), pAGE107 (Cytotechnology, 3, 133 (1990)), pAGE103 (The Journal of Biochemistry, 101, 1307 (1987)), pAMo, pAMoA (pAMoPRSA) (The Journal of Biological Chemistry, 268, 22782-22787 (1993)) or pAS3-3 (JP1990-22705).

Any promoter that can express in a host can be used as a promoter. For example, it is a promoter of IE (Immediate-early) gene of human cytomegalovirus (hCMV), an early promoter of SV40, Long Terminal Repeat Promoter of Moloney Murine Leulemia Virus, a promoter of retrovirus, HSP promoter, SRα promoter or a promoter of metallothionein. An enhancer of IE gene of human CMV can be used with the promoter.

An animal cell as a host is, for example, HEK293 (a human fetal nephrocyte, ATCC:CRL-1573), Namalwa (Burkitt lymphoma, ATCC:CRL-1432), HeLa (a cell of carcinoma of uterine cervix, ATCC:CCL-2), HBT5637 (a leukemia cell, JP1987-299), BALL-1 (a leukemia cell) or HCT-15 (a large bowel cancer cell) of an established cell from a human, Sp2/0-Ag14 (a mouse myeloma cell, ATCC:CRL-1581) or NSO (a mouse myeloma cell) of an established cell from a mouse, COS-1 (African green monkey nephrocyte (SV40 transformed cell), ATCC:CRL-1650) or COS-7 (African green monkey nephrocyte (SV40 transformed cell), ATCC:CRL-1651) of an established cell from a monkey, CHO-K1 (Chinese hamster ovary cell, ATCC:CCL-61) or BHK-21 (C-13) (Sicilian hamster kidney cell, ATCC:CCL-10) of an established cell from a hamster, PC12 (an adrenal pheochromocytoma, ATCC:CRL-1721) or YB2/0 (a rat myeloma cell, ATCC:CRL-1662) of an established cell from a rat.

Any method for introducing DNA into a host can be used as a method for introducing an expression vector. For example, it is an electroporation (Cytotechnology, 3, 133, (1990)), a calcium phosphate method (JP1990-22705) or a lipofection method (Proceedings of the National Academy of Sciences, USA, 84, 7413 (1987) or Virology, 52, 456 (1973)).

(iv) A Case that a Plant Cell is Used as a Host.

When a plant cell or plant is used as a host, a protein of this invention can be produced according to a well-known method (The Tissue Culture, 20 (1994), The Tissue Culture, 21 (1995) or Trends in Biotechnology, 15, 45 (1997)). An expression vector is, for example, Ti plasmid or Tobacco mosaic virus vector. Any promoter that can express in a plant cell can be used as a promoter for a gene expression. For example, it is $^{35}$S promoter of Cauliflower mosaic virus (CaMV) or Rice actin 1 promoter. The expression productivity of a gene can be enhanced by inserting intron 1 of an alcohol dehydrogenase gene of maize between a promoter and expressed gene.

A host is, for example, a plant cell such as potato, tobacco, maize, rice, rape, soybean, tomato, carrot, wheat, barley, rye, alfalfa or flax.

Any method for introducing DNA into a host can be used as a method for introducing an expression vector. For example, it is a method with *Agrobacterium* (JP1983-140885, JP1984-70080 or WO94/00977), an electroporation (JP1984-251887) or a particle gun (gene gun) method (JP2606856, JP2517813).

(v) A Case that an Insect Cell is Used as a Host

When an insect cell is used as a host, an expression vector is, for example, pVL1392, pVL1393 or pBlueBacIII (Invitrogen). A virus for infection is, for example, Baculovirus which infects an insect of *Mamestra brassicoe* family, *Autographa california* nuclear polyhedrosis virus (AcMNPV) or Bac-N-Blue DNA. A method for transforming an insect cell is, for example, a method described in Baculovirus Expression Vector: A Laboratory Manual (1992) (W.H.Freeman and Company), Molecular Cloning: A Laboratory Manual, Second Edition (1989) (Cold Spring Harbor Laboratory Press), Current Protocols in Molecular Biology (1994) (Wiley-InterScience) or Biotechnology, 6, 47 (1988).

An expression vector including a target gene and baculovirus DNA for infection to an insect cell are added into a culture for an insect cell and a virus, which expresses a target gene produced by recombinant, infects an insect cell to express a protein of this invention.

An insect cell as a host is, for example, an established cell from *Spodoptera frugiperda* (*Mamestra brassicoe*) or an established cell from *Trichoplusia ni*. To be more precise, a cell from *S. frugiperda* is Sf9 (ATCC: CRL-1711, an ovary cell), Sf21 (an ovary cell) or the like and a cell strain from *T. ni* is High Five, BTI-TN-5B1-4 (an egg cell, Invitrogen) or the like.

Any method for introducing into a host can be used as a method for introducing an expression vector. For example, it is a calcium phosphate method (JP1990-22705) or a lipofection method (Proceedings of the National Academy of Sciences USA, 84, 7413 (1987)). An electroporation (Cytotechnology, 3, 133 (1990)) can be used as well as an animal cell.

(vi) A Culture Method

When a transformant having an expression vector with an inserted DNA encoding a protein of this invention is a cell such as *Escherichia coli*, yeast, an animal cell or a plant cell, cultivation is held according to a usual culture method suited to all kinds of hosts. The protein is produced, accumulated and collected from a transformant or a culture solution to produce the protein. When a transformant is an animal or a plant, it is breeded or cultured according to a usual growth method suited to all kinds of hosts. The protein is produced, accumulated and collected from the animal or plant to produce the protein.

When a host is an animal, for example, a nonhuman transgenic animal having a gene of this invention is breeded. A protein of this invention encoded in a plasmid is produced and accumulated in the animal and the protein is collected from the animal to produce a protein of this invention. A production/accumulation site in an animal is, for example, milk, sputum or egg of the animal.

When a host is a plant, for example, a transgenic plant having a gene of this invention is cultured. A protein of this invention encoded in a plasmid is produced and accumulated in the plant and the protein is collected from the plant to produce a protein of this invention.

When a host is a prokaryote such as *Escherichia coli* or a eukaryote such as yeast, for example, a transformant having a gene of this invention is cultured in a medium. A protein of this invention encoded in a plasmid is produced or accumulated in the culture solution and the protein is collected from the culture to produce a protein of this invention.

A method for culturing a transformants of a protein of this invention in a medium is accomplished according to a usual method for culturing a host.

As a medium to culture an obtained transformant with a prokaryote such as *Escherichia coli* or a eukaryote such as yeast as a host, a natural or synthetic medium can be used as a medium, if it is a medium including carbon source, nitrogen source and mineral which the host can assimilate and a medium that cultivation of transformants is held efficiently.

When a host is prokaryote such as *Escherichia coli* or a eukaryote, a natural or synthetic medium can be used as a medium that obtained transformants are cultured if it has carbon source, nitrogen source and mineral that a host can assimilate and it is a medium that cultivation of transformants is held efficiently. As a medium when transformants that hosts are *Escherichia coli* are cultured, for example, YT medium including bactotryptone, yeast extract and sodium chloride is preferable.

Any carbon source that each microorganism can assimilate can be used. It is, for example, glucose, fructose, sucrose, syrup including them, carbohydrate such as starch or starch hydrolysate, organic acid such as acetic acid or proprionic acid or alcohol such as ethanol or propanol.

Nitrogen source is, for example, all kinds of inorganic acids such ammonia, ammonium chloride, ammonium sulfate, ammonium acetate, ammonium phosphate, ammonium salts of organic acids, other nitrogenous substances, peptone, meat extract, yeast extract, Corn Steep Liquor, casein hydrolysate, soybean cake, soybean cake hydrolysate, all kinds of fermentative bacteria or the digest.

Mineral is, for example, potassium phosphate monobasic, potassium phosphate dibasic, magnesium phosphate, magnesium sulfate, sodium chloride, ferrous sulfate, manganese sulfate, copper sulfate or calcium carbonate. Cultivation is held under an aerobic condition such as shaking or submerged culture.

Incubation temperature is preferably 15 to 40° C. and culture time is usually 5 hours to 7 days. During cultivation, pH is kept from 3.0 to 9.0. Adjustment of pH is held with mineral or organic acid, alkali solution, urea, calcium carbonate or ammonia. An antibiotic such as ampicillin or tetracycline can be optionally added into a medium during cultivation.

When a microorganism transforming with an expression vector having an inductive promoter is cultured, an inducer can be optionally added into the medium. For example, when a transformant transforming with an expression vector having lac promoter is cultured, isopropyl β-D-thiogalactopyranoside or the like can be added into the medium. When a transformant transforming with an expression vector having trp promoter is cultured, indoleacrylic acid or the like can be added into the medium. A cell and organ of a plant introduced a gene can be done mass culture with jar fermenter. A culture medium is, for example, popularly used Murashige & Skoog (MS) medium, White medium, or the medium added plant hormone such as oxine or cytokinin When a transformant for production of a protein of this invention is an animal cell, a medium for culturing the cell is popularly used RPMI1640 medium (The Journal of the American Medical Association, 199, 519 (1967).), MEM medium (Science, 130, 432 (1959).), D-MEM medium (Virology, 8, 396 (1959).), 199 medium (Proceedings of the Society for the Biological Medicine, 73, 1 (1950).) or the medium added fetal calf serum (FCS).

Cultivation held usually in pH 6 to 8, at 25 to 40° C., in the presence of 5% $CO_2$ for 1 to 7 days. An antibiotic such as kanamycin, penicillin or streptomycin can be optionally added into a medium during cultivation.

When a transformant is an insect cell, a culture medium is popularly used TNM-FH medium (Pharmingen), Sf-900II SFM medium (Invitrogen), ExCe11400, ExCe11405 (JRH Biosciences Inc.), Grace's Insect Medium (Nature, 195, 788 (1962).) or the like.

(vii) A Method for Producing

A protein of this invention can be produced by culturing a transformant, isolating and purifying the protein of this invention from the culture solution. A method for isolating/purifying a protein of this invention can be a usual method widely known in this field. For example, it is a method for isolating/purifying an enzyme or a method for purifying transglucosylase by Sandler (Methods in Enzymology, 83, 458).

When a protein of this invention is produced and accumulated as a dissolved polypeptide, a culture solution in which a transformant is cultured as the above is separated to cells or fungus bodies and a medium, for example, by centrifugal separation. When a protein of this invention exists in a host cell, cells or fungus bodies extracted with an appropriate buffer such as STE solution are washed, broken into pieces by ultrasonic waves, French press, Manton Gaulin homogenizer or Dynomill and separated by centrifugal separation or filtrated to obtain a protein of this invention as acellular solution.

The suitable quantity of surfactant can be included in a buffer for separating/purifying a protein of this invention. For example, sodium lauryl sulfate (SDS) or Sodium N-Dodecanoylsalcosinate (salcosiyl) can be included in the buffer.

A method of separation/purification of target proteins included in obtained crude materials can be accomplished with combination of all kinds of well-known methods of separation/purification. The well-known method is, for example, a solvent extraction method, salting-out method with ammonium sulfate or the like, dialysis, sedimentation with an organic solvent, ultrafiltration method, gel filtration, all kinds of chromatography such as diethylaminoethyl (DEAE)-sepharose chromatography, anion chromatography or ion exchange chromatography using lysine such as DIAION HPA-75 (Mitsubishi Chemical Corporation), cation chromatography using lysine such as S-Sepharose FF (Pharmacia), hydrophobic chromatography using butylsepharose or the like, affinity chromatography or all kinds of electrophoresis such as SDS-polyacrylamide gel electrophoresis or electro-focussing electrophoresis. Affinity chromatography can be accomplished by using an antibody against a protein of this invention.

When a protein of this invention is produced and accumulated as an insoluble protein, cells or fungus bodies are separated as mentioned above and broken into pieces by an appropriate method. Then a division including the polypeptide is collected. A collected sample is solubilized with a solubilizer like a surfactant such as sodium lauryl sulfate (SDS) or Sodium N-Dodecanoylsalcosinate (salcosiyl). After the solubilized solution is diluted or dialyzed to the concentration that a solubilizer is not or almost not included and the polypeptide is constructed to a normal stereo structure, a purification sample can be obtained by a method of separation/purification as mentioned above.

A protein of this invention can be produced as a fusion protein with the other protein and purified by affinity chromatography with a substance having affinity with the fusion protein (Yamakawa Akio, "Experimental Medicine", 13, 469-474 (1995).). An addition protein used as a fusion protein is, for example, protein A or FLAG (Proceedings of the National Academy of Sciences USA, 86, 8227 (1989), Genes Development, 4, 1288 (1990), JP1993-336963 or JP1994-823021). When protein A is used, a fusion protein with a protein of this invention and the protein A can be produced and purified by affinity chromatography with immunoglobulin G. When FLAG peptide is used, a fusion protein with a protein of this invention and FLAG can be produced and purified by affinity chromatography with anti-FLAG antibodies.

A protein of this invention can be produced as well as a well-known method with in vitro transcription/translation system (Journal of Biomolecular NMR, 6, 129-134 (1995), Science, 242, 1162-1164 (1988) or The Journal of Biochemistry, 110, 166-168 (1991)).

A protein of this invention can be chemosynthesized on the basis of the amino acid sequence by a chemical synthesis method such as Fmo method (Fluorenylmethyl oxycarbonyl method) or tBoc method (t-butyl oxycarbonyl method), or peptide synthetic equipment on the market such as, for example, APEX396 (Advanced Chemtech), 433A (Applied Biosystems), PS3 (Protein Technologies), 9050 (Perseptive) or PSSM-8 (Shimazu corporation).

A structural analysis of a protein of this invention can be accomplished by a usual method in the field of protein chemistry, for example, a method described in "A protein structural analysis for gene cloning" (Hisashi Hirano, TOKYO KAGAKU DOZIN Co., LTD., 1993). The activity of a protein of this invention can be measured by a method in Example 3 described below.

(3) A Method of Production of a Variant Polypeptide Mutation

A deletion, substitution or addition of an amino acid of a protein of this invention is accomplished by a site-specific potentially mutagenic method which is a widely known technique. A deletion, substitution or addition of 1 or several amino acid(s) can be prepared as well as the method described in Molecular Cloning: A Laboratory Manual, Second Edition (1989) (Cold Spring Harbor Laboratory Press.), Current Protocols in Molecular Biology (1994) (Wiley-InterScience), Nucleic Acids Research, 10, 6487 (1982), Proceedings of the National Academy of Sciences USA, 79, 6409 (1982), Gene, 34, 315 (1985), Nucleic Acids Research, 13, 4431 (1985), Proceedings of the National Academy of Sciences USA, 82, 488 (1985), Proceedings of the National Academy of Sciences USA, 81, 5662 (1984), Science, 224, 1431 (1984), WO85/00817 or Nature, 316, 601 (1985).

(4) A Production of a Neutralizing Antibody Recognizing a Protein of this Invention (i) A Production of a Polyclonal Antibody A polyclonal antibody can be produced by giving a protein of this invention or a peptide including a part of the protein as an antigen to a mammal. A rabbit, goat, rat, mouse, hamster or the like can be used as a mammal to immunize. A preferable dosage of the antigen is 50 to 100 µg at one time per an animal. In the case of using a peptide, the antigen is preferably covalently bound to a carrier protein such as keyhole limpet haemocyanin or bovine thioglobulin. The peptide of the antigen can be prepared by peptide synthesizer. Administration of the antigen is accomplished 3 to 10 times at interval of 1 to 2 weeks after the first administration. Blood is collected from plexus venosus of ocular fundus at 3 to 7 day after every administration so as to confirm that the serum reacts with the used antigen by an enzyme immunoassay (enzyme immunoassay (ELISA method): published by Igakushoin (1976), Antibodies-A Laboratory Manual, Cold Spring Harbor Laboratory (1988)) or the like.

The serum is collected from non-human immunized mammals and the antibody titer against the antigen is measured. The serum is collected at the time when sufficient antibody titer is obtained, and then the polyclonal antibody can be isolated and purified from the serum by the following method. Isolation or purification of an antibody is carried out by one or combination of methods such as centrifugal separation, salting out with 40-50% saturated ammonium sulfate, caprylic acid precipitation (Antibodies, A Laboratory manual, Cold Spring Harbor Laboratory, (1988)) or chromatography with DEAE-sepharose column, anion exchange column, protein A column, G-column, gel filtration column or the like.

(ii) A Production of a Monoclonal Antibody (a) A Preparation of an Antibody Producing Cell A mouse or rat whose serum has sufficient antibody titer to a polypeptide fragment of the protein of this invention used to immunize is provided as a source of supply of an antibody producing cell.

The spleen is collected at 3 to 7 days after an antigenic substance is administrated last to a rat whose has sufficient antibody titer. The spleen is macerated in a MEM culture medium (Nissui Pharmaceuticals Co.), appeased with a dressing forcep and centrifuged at 1,200 rpm for 5 min. The supernatant is removed. The obtained precipitate is treated with Tris-ammonium chloride buffer (pH 7.65) for 1 to 2 min, to remove erythrocyte, and then washed with a MEM culture medium three times to give the spleen cell as an antibody-forming cell.

(b) A preparation of a Myeloma Cell

An established cell line from a mouse or rat is used as a myeloma cell. For example, it is a myeloma cell of 8-azaguanine resistance mouse (from BALB/c), P3-X63Ag8-U1 strain (described blow as P3-U1) (Current Topics Microbiological Immunology, 81, 1 (1978) or European Journal of Immunology, 6, 511 (1976)), SP2/0-Ag14 strain (described blow as SP-2) (Nature, 276, 269 (1978)), P3-X63-Ag8653 strain (described blow as 653) (Journal of Immunology, 123, 1548 (1979)) or P3-X63-Ag8 (described blow as X63) (Nature, 256, 495 (1975)). These cell strains are subcultured in a 8-azaguanine medium (a normal medium including 15 µg/ml 8-azaguanine (RPMI1640 medium including 1.5 mM glutamine, $5 \times 10^{-5}$ M 2-mercaptoethanol, 10 µg/ml gentamysin and 10% FCS made by CSL)) and cultured in a normal medium for 3 to 4 days before cell fusion. $2 \times 10^7$ or more cells are prepared for cell fusion.

(c) A Production of Hybridoma

Antibody producing cells prepared in (a) and myeloma cells prepared in (b) are washed with MEM medium or PBS (1.83 g sodium phosphate dibasic, 0.21 g monobasic potassium phosphate, 7.65 g NaCl, 1 L distilled water, pH 7.2) and mixed as the number of antibody producing cells is 5 to 10 times larger than that of the myeloma cells. After centrifugal separation at 1,200 rpm for 5 minutes, supernatant is removed. The cells in an obtained precipitated fraction are well separated and 0.2 to 1 ml of a mixture solution of 2 g polyethylene glycol-1000 (PEG-1000), 2 ml MEM medium and 0.7 ml dimethyl sulfoxide (DMSO) per $10^8$ antibody producing cells is added to the cells with stirring at 37° C. And then 1 to 2 ml of MEM medium is added for several times every 1 to 2 minutes. The solution is prepared with MEM medium to 50 ml in total. After centrifugal separation at 900 rpm for 5 minutes, supernatant is removed. After the cells in an obtained precipitated fraction are slowly separated, the cells are slowly suspended in 100 ml of HAT medium (a normal medium including $10^{-4}$ M hypoxanthine, $1.5 \times 10^{-5}$ M thymidine and $4 \times 10^{-7}$ M aminopterin) by sunction and blow-off of a measuring pipet.

The suspension is poured into the 96-well culture plate at 100 µl per well and cultured at 37° C. in the presence of 5% $CO_2$ for 7 to 14 days. After culturing and obtaining a part of culture supernatant, a hybridoma specifically reacting with a part of a polypeptide fragment of a protein of this invention is selected by an enzyme immunoassay described in Antibodies (A Laboratory Manual, Cold Spring Harbor Laboratory, Chapter 14 (1988)) or the like.

This invention also relates to a method for screening an angiogenesis inhibitor or promoter. The method for screening is characterized by detecting or measuring change of a protein or a gene of this invention under the presence of a test substance or the salt.

More specifically, a substance used as an angiogenesis inhibitor or promoter is efficiently screened by measuring the effect of a test substance on the change of a protein or gene of this invention having angiogenesis inhibitory activity. The effect of a test substance on the change of a protein or gene of this invention is preferably measured by using the change of the protein or gene under the absence of a test substance as a reference.

Additionally, a method for screening of this invention can be used for pharmacological estimation of a candidate compound as an angiogenesis inhibitor or promoter.

A compound or the salt as the above test substance is a low-molecular compound, a high-molecular compound, a polypeptide, a derivative thereof, a nucleic acid, a derivative thereof or the like. The compound or the salt can be a natural or unnatural substance. The derivative of a polypeptide is a modifying polypeptide obtained by adding a modifying group, a variant polypeptide obtained by reforming an amino acid residue or the like. The derivative of a nucleic acid is a modifying nucleic acid obtained by adding a modifying group, a variant nucleic acid obtained by reforming a base, a peptide nucleic acid or the like. A nucleic acid includes siRNA which can induce RNAi against a gene of this invention, antisense RNA, ribozyme or the like.

A method for screening of this invention is performed by detecting or measuring "the change of a protein or a gene of this invention".

"The change of a protein or a gene of this invention" detected or measured in a method for screening of this invention is, for example, presence or absence of the binding between the protein and the ligand; expression of the gene, in particular, presence or absence of the expression, the change of the expression or the like.

As a method for screening of this invention, there are three embodiments in general terms according to "the change of a protein or a gene of this invention" of a target for detecting or measuring.

The first embodiment of a method for screening of this invention is a method comprising, (I) a step for contacting a protein of this invention with a test substance, and (II) a step for detecting the binding between the protein and the test substance after the above step (I) and selecting the test substance which binds to the protein as a candidate compound of an angiogenesis inhibitor or promoter.

With this method, a substance which effects on the function of the protein through the binding to the above protein can be selected. Therefore, the candidate compound selected has a character that it directly and specifically binds to the above protein and regulates the function.

A protein of this invention used in this embodiment includes the protein itself, a partial peptide thereof; a protein having an amino acid sequence of the above protein with at least 1 amino acid mutation and equivalent activity of the above protein, a partial peptide thereof or the like.

In the above step (I), contacting the above protein and a test substance can be performed by mixing the above protein with a test substance, for example, in a solution which does not prevent the natural functions of the protein and maintaining the mixture under an appropriate reaction condition (e.g., reaction temperature or reaction time) (to react the protein with the test substance).

The above "a solution which does not prevent the natural functions of the protein" is, for example, phosphate-buffered saline (PBS), HEPES buffer, Tris buffer or the like.

The reaction condition in step (I) is not especially restricted, for example, in the above solution usually at pH 6.0-10.0, preferably pH7.0-9.0, more preferably pH7.5-8.5 and much more preferably pH8.0, usually at 10-50° C., preferably 20-40° C., more preferably 25-37° C. and much more preferably 25° C., usually for 1 minute-1 hour, preferably for 3-30 minutes, more preferably for 5-20 minutes and much more preferably for 10 minutes.

Next, in step (II), presence or absence of the binding between the above protein and the test substance is checked by detecting it.

The binding can be detected, for example, by reacting the above protein with, for example, a test substance labeled with a radioactive substance in step (I) as the above and analyzing radioactivity of the protein in the solution under competition with overpresence of nonradioactive test substances. Furthermore, the change of the activity of a protein of this invention can be detected by a method for measuring cell stimulatory activity, for example, activity to promote or inhibit DNA synthesis by bringing BrdU (bromodeoxyuridine), cell migrating activity or the like with binding to a protein of this invention, or a method for measuring visually network formation of vascular endothelial cells with microscope or the like. When the change of the activity is detected, the test substance used is selected as a candidate compound of an angiogenesis inhibitor or promoter.

Step (I) and (II) can be performed as a consecutive step. This embodiment can be performed, for example, by a binding assay to a carrier having a test substance or the like.

The second embodiment of a method for screening of this invention is a method comprising, (I') a step for contacting a protein of this invention with a test substance under the presence of a binding substance of a protein of this invention, and (II') a step for detecting the bonding amount of the protein and the binding substance after the above step (I') and selecting the test substance which changes the bonding amount of the protein and the binding substance as a candidate compound of an angiogenesis inhibitor or promoter.

With this method, a substance which effects on the function of the protein by inhibiting or promoting the binding between the protein and the above binding substance can be selected. Therefore, the candidate compound selected has a character that it plays a role in the binding between the protein and the above binding substance and regulates the protein. A candidate compound selected as above includes (a) a substance which enhances or reduces cell stimulatory activity through the binding between a protein of this invention and a binding substance, for example, activity to promote or inhibit DNA synthesis by bringing BrdU (bromodeoxyuridine) or cell migrating activity or the like, (b) a substance which enhances or reduces bonding strength between a protein of this invention and a binding substance, or the like.

A protein of this invention, reaction condition or the like used in this embodiment is the same as that in the above first embodiment.

The bonding amount can be detected, for example, by reacting the protein of the invention with a test substance under the presence of the above binding substance labeled with radioactive substance in step (I') as the above and analyzing radioactivity of the binding substance in the solution under competition with overpresence of nonradioactive test substances. For example, it is characterized by measuring cell stimulatory activity or the like and comparing. When the change of the bonding amount is detected, the test substance used is selected as a candidate compound of an angiogenesis inhibitor or promoter.

The third embodiment of a method for screening of this invention is a method comprising, (I") a step for introducing a gene of this invention into a cell, (II") a step for expressing the above gene in the cell obtained in the above step (I") under the presence of a test substance, and (III") a step for detecting presence or absence of expression of the above gene or measuring the change of expression of the above gene with comparing it with that under absence of the test substance and selecting the test substance which changes expression of the gene as a candidate compound of a angiogenesis inhibitor or promoter.

In the above step (I"), introducing a gene of this invention into a cell is preferably performed, for example, with a nucleic acid construction having the gene operatively linked to downstream and under the control of a regulatory element for expression known as a regulatory domain for expression of the gene. The above regulatory element for expression is described in, for example, Oncogene, 1996, Vol. 13, 143-149.

The above "a nucleic acid construction" can be easily constructed by inserting the above regulatory element for expression and a gene of this invention into a cloning site of a commonly-used expression vector. This vector is, for example, a virus vector, a plasmid vector or the like.

A gene of this invention used in this embodiment includes the gene itself; a gene hybridizing under a stringent condition with antisense strand of the above gene and encoding a protein having equivalent activity to a protein of this invention; a gene having a base sequence of the above gene with at least 1 base mutation and encoding a protein having an equivalent activity to the above protein; a gene having homology of at least 60%, preferably 80% or more and more preferably 90% or more with a base sequence of the above gene and encoding a protein having equivalent activity to a protein of this invention or the like.

For the above nucleic acid construction, a gene, which can be able to determine quantity of the translation product, such as chloramphenicol acetyltransferase, (β-galactosidase or luciferase can be used as a substitution for a gene of this invention.

In case that expression of a gene of this invention is essential because of the construction of the embodiment in the various embodiments of this invention, a vector used for expression of this gene, a host cell to introduce a nucleic acid construction or the like can be derived from any species as long as expression of the above gene can be accomplished with the arbitrary combination of them. Examples and a method for introducing the above nucleic acid construction into a cell, a method for culturing a transformant introduced the above nucleic acid construction or the like is the same as the description as to a transformant in a method for producing the above protein. Considering that a gene of this invention is derived form eukaryote and that a therapeutic or preventive agent which this invention provides or the like can be preferably used for eukaryote, mammal, especially human, a host cell used for the above gene is preferably an animal cell.

In this embodiment, step (I") can be omitted if the above stable cell line introduced a nucleic acid construction is used.

Next, in step (II"), a gene of this invention is expressed in the cell obtained in the above step (I") under the presence of a test substance.

This step can be performed by culturing a cell obtained in the above step (I"), for example, in a medium containing a test substance. Culture condition is the same as that for transformant in the above method for producing the protein of this invention.

Next, in step (III"), presence or absence of expression of the above gene is detected or the change of expression of the above gene is measured comparing to the case under the absence of a test substance, and then, a test substance which effects on the change of expression of the gene is selected as a candidate compound of an angiogenesis inhibitor or promoter.

"The case under the absence of a test substance" means a case that the cell obtained in step (I") maintains under the absence of a test substance to express the above gene in step (II"). It is a criterion for understanding the change of expression of the above gene under the presence of the test substance. To be more precise, a cell, extract of the cell or the like is used as a control.

When the change of expression of the above gene is recognized compared to a control as a result of detecting presence or absence of the expression or measuring the change of the expression, for example, when expression of the above gene is recognized in control, and expression level of expression of the above gene in a cell contacting with a test substance is increasing compared to a control, that is to say, when expression of the above gene is increasing compared to a control, the a test substance is decided and selected as a candidate compound of an angiogenesis inhibitor. For example, when expression of the above gene is recognized in control, and expression of the above gene in a cell contacting with a test substance is not detected or expression level of the expression is decreasing compared to a control, that is to say, when expression of the above gene is decreasing compared to a control, the test substance is decided and selected as a candidate compound of an angiogenesis promoter.

The candidate compound selected is thought to have a characteristic property that it promotes or inhibits expression of the above gene in a cell at transcriptional level and, shows the beneficial effect to be able to specifically promote or inhibit expression of the above gene.

Detection of presence or absence of expression of the gene or measurement of the change of expression is preferably performed with amount of mRNA of the gene or the protein as an indicator. Any molecular-biological assay detecting mRNA or immunoassay detecting a protein can be used. A molecular-biological assay is, for example, polymerase chain reaction (PCR), Northern blot, Dot blot or an analysis method with microarray or macroarray. An immunological assay is, for example, ELISA with a microtiter plate, RIA, a fluorescence antibody technique, Western blotting or an immune structure dyeing method. They are described in detail below.

(1) A Molecular-Biological Assay

Amount of expression of DNA encoding a protein of this invention can be determined by measuring mRNA with oligonucleotide(s) prepared from a gene of this invention by northern hybridization or RT-PCR.

When mRNA from a transformant expressing a protein of this invention or the partial peptide is determined quantity, mRNA can be extracted from the transformant by a well-known and commonly-used method in this field, determined quantity and analyzed by RT-PCR, northern blotting, northern hybridization or the like.

"Primer pair" for PCR is a primer pair consisting of a primer corresponding to a sense sequence of 5'-end and a primer corresponding to an antisense sequence of 3'-end of a nucleic acid encoding a protein of this invention or a nucleic acid consisting of a specific sequence part of the nucleic acid or the like. This primer pair can be appropriately selected considering operability when it is used and according to an appropriate Tm value, second structure or the like. In particular, the primer pair which can amplify all of a base sequence described in SEQ ID: 1, 3, 5, 7 or 9 or the specific sequence part is preferable. In more particular, it is, for example, a primer pair selected from the group consisting of a nucleic acid having base sequence described in SEQ ID: 1, 3, 5, 7 or 9. Example of the primer pair is not restricted, for example, a primer pair of SEQ ID: 13 and 14. The primer can be labeled with commonly-used fluorescent dye, radioactive substance or the like. Detection of amplification products can be performed by visibilitization with ethidium bromide or a fluorescent substance, or detection with a labeled primer in commonly-used agarose gel electrophoresis or the like.

When Northern blotting is used, hybrid formation or the amount in a test sample obtained from a test object is measured, for example, with a probe detecting a nucleic acid encoding a protein having the above amino acid sequence selected from the group consisting of SEQ ID NO: 2, 4, 6, 8 and 10 or a protein having the amino acid sequence with 1 or several amino acid(s) deletion, substitution or addition comparing to the result in a control sample, and then expression level of a gene encoding a protein of this invention can be evaluated.

When an analysis method with microarray or macroarray is used, hybrid formation or the amount in a test sample obtained from a test object is measured, for example, by using microarray or macroarray with at least one or more probe(s) detecting a nucleic acid encoding a protein having the above amino acid sequence selected from the group consisting of SEQ ID NO: 2, 4, 6, 8 and 10 or a protein having the amino acid sequence with 1 or several amino acid(s) deletion, substitution or addition to the result in a control sample, and then expression level of a gene encoding a protein of this invention can be evaluated.

"A probe" used for Northern blotting or an analysis method with microarray or macroarray is, for example, a nucleic acid used for detecting a nucleic acid consisting of a base sequence selected from the group consisting of SEQ ID: 1, 3, 5, 7 and 9. A nucleic acid used for a probe can be appropriately selected considering operability when it is used and according to an appropriate Tm value, second structure or the like. The nucleic acid can be labeled with commonly-used fluorescent dye, radioactive substance or the like.

(2) An Immunological Assay of a Protein of this Invention

An immunological assay of a protein of this invention is, for example, a method to measure the protein or the partial peptide with a marker which an antibody against the protein or the partial peptide is directly or indirectly bonded to enzyme, fluorescent substance, radioisotope, latex or the like. The assay is, for example, ELISA or a chemiluminescence method detecting with enzyme labeling such as horseradish peroxidase or alkaline phosphatase, FITC method detecting a fluorescent tag such as luminol or GFP (Green Fluorescence Protein), RIA method detecting a radioisotope tag such as $^{125}$I or a latex agglutination method detecting binding with latex.

The measuring method is, for example, Western blotting and an immune structure dyeing method or the like.

Furthermore, a protein of this invention or the partial peptide can be determined quantity by the measuring method.

An antibody for an immunoassay can be immobilized to a solid phase carrier and a trapped polypeptide can be detected by using a secondary antibody with a reporter group or using a reagent. A competitive method that a protein of this invention is labeled with a reporter group, reacted with an antibody and a sample and bonded with an immobilized antibody can be used to detect. The level of inhibition the binding between a labeled polypeptide and an antibody by a protein of this invention of a sample is shown by reactivity with an immobilized antibody of a sample and the concentration of a protein of this invention in a sample can be calculated. Any substance, to which an antibody can attach and which is widely known to a parson having ordinary skill in the art, can be used as a solid phase carrier. The substance includes, for example, a microtitre plate, a membrane such as a nitrocellulose membrane, bead, disk, glass, glass fiber, plastic material such as latex, polystyrene or polyvinyl chloride. Magnetic particle or fiber optical sensors (U.S. Pat. No. 5,359,681 or the like) can be also used. A well-known method used in this field can be used as a method for immunobilizing an antibody to a carrier. In this description, "solid phase" means immobilization by a physical method such as adsorption or chemical binding by a covalent bond between an antibody and a functional group on a carrier. An antibody and a functional group on a carrier can be bonded directly or through a cross-linking agent.

Immobilization by a physical method can be accomplished by contacting an antibody appropriately diluted in an appropriate buffer with a carrier, preferably, a microtiter plate or a membrane for an appropriate time. The contact time varies depending on temperature, but it is typically between about 1 hour and 1 day. About 10 ng to 1 µg, preferably, about 100 to 200 ng of an antibody is added and immobilized on each well of a microtiter plate made of plastic such as polystyrene or polyvinyl chloride.

Immobilization by a chemical method can be accomplished by reacting a carrier and functional groups of an antibody, for example, a reaction of a carrier and a two-functional reagent that reacts with both hydroxyl groups and amino groups and a carrier. For example, antibody can be immobilized to a carrier having an appropriate polymer coat with a covalent bond by using benzoquinone or condensation between aldehyde groups on a carrier and an amine or an active hydrogen on a combination partner. The method can be accomplished, for example, according to Pierce Immunotechnology Catalog and Handbook (1991) A12-A13.

A carrier-immobilized antibody is treated to inhibit physical adsorption of other polypeptides by a well-known method for a parson having ordinary skill in the art with an appropriate blocking reagent, for example, cattle serum albumin or Tween 20 (Sigma-Aldrich).

A carrier-immobilized antibody is reacted with a sample, and a protein of this invention and an antibody are combined. A sample can be appropriately diluted with an appropriate diluent, for example, PBS. Reaction time of a sample and antibody should be enough to detect the presence of a protein of this invention in a sample, preferably, time to achieve at least 95% of binding level compared to the level at which bound and not-bound polypeptide are equilibrated. Time to reach to equilibrium can be easily decided by measuring the binding level by the time. Substances other than bound polypeptide can be removed by washing a solid carrier with an appropriate buffer, for example, PBS (including 0.1% Tween 20). Labeled secondary antibodies are reacted with a solid carrier. The label is preferably an enzyme such as horseradish peroxidase, a ground substance, a supplemental element, an inhibitor, a pigment, a radioisotope, a coloring substance, a fluorescent substance or the like. The binding between an antibody and a label can be accomplished by a well-known method for a parson having ordinary skill in the art. The secondary antibody is reacted for sufficient time to bind to complexes, which include an immobilized antibody and a protein of this invention. Appropriate time can be easily decided by measuring binding level by the time. The non-binding secondary antibody can be removed by washing a solid carrier with an appropriate buffer, for example, PBS (including 0.1% Tween 20). The method of detection of a label of the secondary antibody is different according to a kind of labels. When a radioisotope is used as a label, detection by scintillation counter or autoradiography can be used. When a pigment, coloring substance or fluorescent substance is used as a label, detection by spectrophotometer can be used. When enzyme is used as a label, a ground substance against the enzyme is added and reacted for fixed time and the product is detected by spectrophotometer. A label and secondary antibody can bind directly or indirectly by an avidin-biotin method. When they bind indirectly, one part of the avidin-biotin is bound to a secondary antibody and another is bound to a label.

"A kit for screening" of this invention includes at least a protein of this invention, a part thereof, a gene of this invention, a part thereof, a nucleic acid construction having the gene, a cell introducing the gene, an antibody against a protein of this invention, or the like.

A kit for screening of this invention is, for example, a kit comprising a protein of this invention, a kit comprising a nucleic acid construction comprising a gene of this invention, a kit comprising a cell introducing a gene of this invention, or a kit comprising an antibody against a protein of this invention or a fragment thereof.

The above probe and/or primer pair preferably used for a method for screening of this invention can be included in each kit, if desired. Furthermore, a detection reagent, buffer, standard substance, manual for performing a method for screening of this invention or the like can be included, if desired.

An angiogenesis inhibitor or promoter comprising at least one selected from a protein of this invention, neutralizing antibody of this invention, compound obtained by the above method for screening or a kit for screening or the like can be single administrated as a preventive or therapeutic agent. However, it is usually preferred that it is mixed with one or more pharmaceutically acceptable carrier(s) and provided as a pharmaceutical preparation produced by any method which is well-known in a technical field of galenical pharmacy. An angiogenesis inhibitor or promoter of this invention has a preventive or therapeutic effect on an angiogenesis related disease through expression of a protein of this invention (having angiogenesis inhibitory activity) or effects on expression of the protein (for example, promoting or inhibiting effect on the expression).

An angiogenesis inhibitor or promoter of this invention can additionally comprise different auxiliaries which can maintain stably the above protein, neutralizing antibody or compound. To be more precise, it is a pharmaceutical acceptable auxiliary with the character that it inhibits degradation of the active ingredient before reaching a site which is an object to send the active ingredient. For example, it is an excipient, binding agent, stabilizing agent, buffer agent, solubilizing agent, isotonic agent or the like.

An excipient which can be mixed to a tablet, a capsule or the like is, for example, a binding agent such as gelatin, corn starch, traganth or Arabian gum, a vehicle such as crystalline cellulose, a swelling agent such as corn starch, gelatin or alginic acid, a lubricant such as magnesium stearate, a sweetening agent such as saccharose, lactose or saccharin, a flavoring agent such as peppermint, oil of wintergreen or cherry. When preparation unit is a capsule, a liquid carrier such as fat can be also comprised except for the above materials. An aseptic composition for injection can be prescribed according to a usual preparation method that the active substance is dissolved or suspended in vehicle such as injectable water, natural plant oil such as sesame oil or coconut oil, or the like. Aqueous liquid for injection is, for example, a physiological salt solution or isotonic solution of D-sorbitol, D-mannitol, sodium chloride or the like comprising dextrose or adjuvant and can be used with an appropriate solubilizing agent, for example, an alcohol such as ethanol, propylene glycol or polyethylene glycol or a nonionic surfactant such as polysorbate 80 or HCO-50. Oil is, for example, sesame oil, soy oil or the like and can be used with a solubilizing agent such as benzyl benzoate or benzyl alcohol.

The above angiogenesis inhibitor or promoter can be mixed with, for example, a buffer such as a phosphate buffer or sodium acetate buffer, a soothing agent such as benzalkonium chloride or procaine hydrochloride, a stabilizer such as human serum albumin or polyethylene glycol, a preservative such as benzyl alcohol or phenol, or an oxidation inhibitor. A prepared parenteral solution is usually filled up an appropriate ampoule. Because a preparation obtained as above has safety and low toxicity, it can be administrated to, for example, mammal such as human, rat, mouse, rabbit, sheep, pig, cattle, cat, dog or monkey.

The most effective route of administration in treats is desirable as a route of administration, for example, an oral administration or non-oral administration such as intraoral, tracheobronchial, intrarectal, subcutaneous, intramuscular or intravenous. A form of administration is, for example, spray, capsule, tablet, granule, syrup, emulsion, suppository, injection, ointment or tapes.

An appropriate pharmaceutical preparation for an oral administration is, for example, emulsion, syrup, capsule, tablet, powder or granule. For example, a liquid preparation such as emulsion or syrup can be produced with water, saccharide such as sucrose, sorbitol or fructose, glycol such as polyethylene glycol or propylene glycol, oil such as sesame oil, olive oil or soybean oil, antiseptic such as p-hydroxy ester benzoate or flavor such as strawberry or peppermint as an excipient. Capsule, tablet, powder or granule can be produced with a vehicle such as lactose, dextrose, sucrose or mannitol, a disintegrating agent such as starch or sodium alginate, a lubricant such as magnesium stearate or talc, a binding agent such as polyvinyl alcohol, hydroxypropylcellulose or gelatin, a surface active agent such as fatty acid ester or a plasticizer such as glycerol as an excipient.

An appropriate pharmaceutical preparation for non-oral administration is, for example, injection, suppository or spray. For example, an injection is prepared with a carrier comprising salt solution, dextrose solution or their mixture. A suppository is prepared with a carrier such as cacao butter, fat hydride or carboxylic acid. A spray is prepared with the substance or a carrier, which does not stimulate oral cavity and airway mucous membrane of a recipient and spread the substance as microparticles to become easy to absorb. The carrier includes, for example, lactose or glycerol. A pharmaceutical preparation such as aerosol or dry powder is possible if a nature of the substance and that of the used carrier are appropriate for it. And in these non-oral agents, a component used as an excipient in oral agents can be added.

The dosage of an angiogenesis inhibitor or promoter of this invention is also suitably selected depending on a kind of an active ingredient; an individual, organ, local part or organization which is an object of administration; the age or body weight of an individual who is an object of administration or the like. The dosage is not especially restricted. It is one time or at few times per 1 day. The dosage of the active ingredient at one time is, for example, 0.0001-1000 mg/kg weight and preferably 0.001-100 mg/kg weight when the active ingredient is a low-molecular or high-molecular compound. It is, for example, 0.0001-1000 mg/kg weight and preferably 0.001-100 mg/kg weight when the active ingredient is a polypeptide or the derivative. It is, for example, 0.00001-100 mg/kg weight and preferably 0.0001-10 mg/kg weight when the active ingredient is a nucleic acid or the derivative. The administration period is not especially restricted.

Pharmacological evaluation of an angiogenesis inhibitor or promoter of this invention can be performed by a method comprising a step for administrating an angiogenesis inhibitor or promoter of this invention to, for example, a mouse model for an angiogenesis related disease, and a step for evaluating with an indicator which is the case that recovery from an angiogenesis related disease in an administrated animal comparing to a non-administrated animal is shown.

An angiogenesis inhibitor or promoter of this invention can be used by adding to food or feed. "Food" or "feed" means a natural product comprising one kind or more of nutriment(s) or a manufactured good thereof and includes all kinds of food and drink Food and feed mixed with an angiogenesis inhibitor or promoter of this invention is useful as a health supplement for prevention and/or therapy of an angiogenesis related disease.

An expression vector for inhibiting or inducing angiogenesis comprising at least one selected from a gene of this invention, a compound obtained by using the above method for screening or kit for screening (nucleic acid or the derivative) or the like, has a therapeutic or preventive effect on an angiogenesis related disease.

A method for producing an expression vector of this invention, a method for expressing in a cell or the like is the same as an expression vector described in the above "a method for obtaining a gene of this invention" and "a method for producing this protein".

Because an expression vector of this invention has safety and low toxicity, it can be administrated to, for example, mammal (for example, human, rat, mouse, rabbit, sheep, pig, cattle, cat, dog or monkey). When it is used for gene therapy, a DNA or RNA virus vector or a plasmid vector which can express a protein in a cell of a mammal such as human and has high safety is preferably used. A virus vector preferably used for gene therapy is adenovirus, adeno-associated virus (AAV), retrovirus, poxvirus, herpesvirus, herpes simplex virus, lentivirus (HIV), Sendai virus, Epstein-Barr virus (EBV), vaccinia virus, poliovirus, Sinbis virus, SV40 or the like. A plasmid preferably used for gene therapy is pCAGGS [Gene, 108, 193-200 (1991)], pBK-CMV, pcDNA 3.1, pZeoSV (Invitrogen or Stratagene) or the like.

A method for introducing an expression vector of this invention to a patient is in vivo method that the vector is directly induced inside the body or ex vivo method that DNA is induced into a kind of a cell obtained from human outside the body and the cell is returned inside the body [Nikkei Science, April, 20-45 (1994), Gekkan-Yakuji, 36, 23-48 (1994), Jikken-Igaku, special issue, 12, 15 (1994)]. In this invention, in vivo method is preferable.

When in vivo method is used, an appropriate route of administration according to a disease of a therapeutic purpose, a target organ or the like is used. For example, it can be to select a direct local administration to a tissue with lesion, or an intravenous, intra-arterial, subcutaneous, intramuscular, intraabdominal, endoscopically or aerosol administration. As a medication method, intravenous or intraabdominal administration is preferable. Additionally, a direct injection to a tissue with lesion is preferable. A tissue with lesion is taken a picture with any imaging used in this technical field such as Magnetic Resonance Imaging or Computed Tomography and a vector of this invention can be administrated, for example, by stereotaxic injection.

DNA encoding a protein of this invention is turned to be a secretory protein by adding a signal sequence. In this case, it needs not necessarily local administration. A protein produced and secreted in a cell can have effect on remote target organ and generate angiogenesis inhibitory activity. Therefore, it can be also administrated to a normal tissue except for pathologic tissues, or normal cell. When it is administrated to a human, intravenous administration or intramuscular administration is preferable.

A form of formulation of a vector of this invention (a gene therapy agent) can be one of different forms according to the above each form of administration. For example, when it is an injection comprising DNA of this invention which is an active ingredient, the injection can be prepared by a usual method. A base ingredient for a gene therapy agent is not especially restricted as long as it is a base ingredient usually used for an injection. It is, for example, distilled water, sodium chloride, a salt solution such as mixture of sodium chloride and mineral salts, a solution such as mannitol, lactose, dextran or glucose, an amino acid solution such as glycine or arginine, or mixture of an organic acid solution or a salt solution and a glucose solution. An injection can be prepared with an auxiliary such as an osmotic adjustment agent, pH adjustment agent, plant oil such as sesame oil or soybean oil, surfactant such as lecithin or nonionic surfactant or the like according to a usual method as a solution, suspension or dispersion. The injection as above can be a preparation dissolved in use by manipulation such as disintegration or lyophilization.

Content of DNA of a preparation is different depending on a disease of therapeutic purpose, administration site, number of doses, desired duration of therapy, an age or body weight of a patient or the like and can be suitably adjusted. It is usually about 0.01-2000 mg and preferably 0.1-100 mg of DNA encoding a protein of this invention for a patient (the body weight is 60 kg).

The following examples are provided to exemplify and do not restrict the present invention. As a genetic engineering method, the method described in Molecular Cloning: *A Laboratory Manual*, 2nd Edition (Cold Spring Harbor Laboratory) is used if there is not a special provision.

EXAMPLE 1

Search of a Homologous Gene of an Angiogenesis Inhibitor, Vasohibin

To search for a structural analogous gene of an angiogenesis inhibitor which we have found, Vasohibin (J. Clin. Invest., 114 (7), 898-907, 2004), homology search of an amino acid which the same sequence can encode was performed based on a base sequence of Vasohibin cDNA (KIAA1036, Acc# NM_014909, SEQ ID: 11) with Blastx search in AssEST (Maze, Inc.) which is EST cluster data base. It became clear that Vasohibin protein (SEQ ID: 12) has 58% homology with AK022567 protein (SEQ ID: 2). Furthermore, homology search was performed based on this base sequence of AK022567 gene (SEQ ID: 1) with a database of NCBI (National Center for Biotechnology Information) in U.S. and BC051856 (SEQ ID: 3), BC053836 (SEQ ID: 5) and BC028194 (SEQ ID: 7) which have been respectively registered as a gene encoding a protein whose function is unknown, FLJ 12505 were found. Base sequences of these three genes and AK022567 gene were searched with human genome database Ensembl and it became clear that each of these genes exists on the long arm of first chromosome, 1q32.3 and they were 4 variants generated by selective splicing. AK022567 was named Variant 1, BC051856 was named Variant 2, BC053836 named was Variant 3 and BC028194 named was Variant 4 (FIG. 1).

Whether a gene of this invention was expressed in HUVEC (human umbilical vein endothelial cells) as Vasohibin or not was confirmed by RT-PCR with primers consisting of SEQ ID: 13 and 14, and DNA fragment larger than expected from Variant 1, 2, 3 and 4 was found. A base sequence of the DNA fragment (SEQ ID: 9) was determined and it became clear that the fragment was produced by new selective splicing. This was named Variant 5 (FIG. 1). Among 5 variants, an amino acid sequence (SEQ ID: 10) encoded in Variant 5 is highest homology with an amino acid sequence of Vasohibin (FIG. 2).

EXAMPLE 2

Expression and Preparation of a Protein of this Invention by Using Baculovirus cDNA encoding the polypeptide that 3×FLAG sequence was added to carboxy-terminal of Variant 1 was inserted to a expression vector in an insect cell, pFASTBac1 (Invitrogen), to construct an expression plasmid in a insect cell, pFASTBac1036. Bac-To-Bac Baculovirus Expression Systems (Invitrogen) was used for expression in an insect cell and manipulation or the like was performed according to an attached manual. More specifically, DH10Bac *E. coli* was transformed with a constructed pFASTBac1036 plasmid to obtain a recombinant Bacmid DNA. Next, gene introduction of this Bacmid DNA into a Sf9 cell was performed with CELLFECTIN reagent (Invitrogen) to obtain a recombinant baculovirus. This virus solution 0.5 ml was used at a rate that it infected 50 ml of Sf9 cells with concentration of $1.5 \times 10^6$/ml. After infection, it cultured for 96 hours and the cells were collected by centrifugation.

Identification of expression a protein of this invention with FLAG in an insect cell was performed by Western blotting with extract of the Sf9 cell and anti-FLAG M2 mAb antibody labeled with HRP (SIGMA). At first, the cells were washed with 5 mL of phosphate buffered saline (PBS) and suspended in 5 ml of Lysis reagent (50 mM Tris-HCl including 0.15 M NaCl, 0.1 mM EDTA, 0.1 mM EGTA, 1 mM DTT, 0.1 mM amidinophenyl methansulufonyl fluoride hydrochloride or 0.1% NP-40, pH 7.4). After ultrasonication under cooling with ice for 15 seconds at 4 times with MICROCON (HEART SYSTEMS), centrifugation at 14,500×g for 20 minutes was performed. The same amount of Lysis reagent was added to the supernatant to make it a lysate solution. Western blotting was performed by separating 0.5 µl solution with SDS-PAGE according to the method of Laemli, electrically transferring on a nitrocellulose membrane (TEFCO), blocking in TBS including 5% skim milk and reacting with anti-FLAG M2 mAb labeled with HRP. After washing with TBS (Tris-HCl including 0.15 M NaCl, pH 7.4) for 10 minutes at 3 times, results were visualized by chemiluminescence with ECL- Plus reagent (Amersham Pharmacia) and Hyper film ECL film (Amersham Pharmacia) was exposed to the light to detect them.

Figure 3:
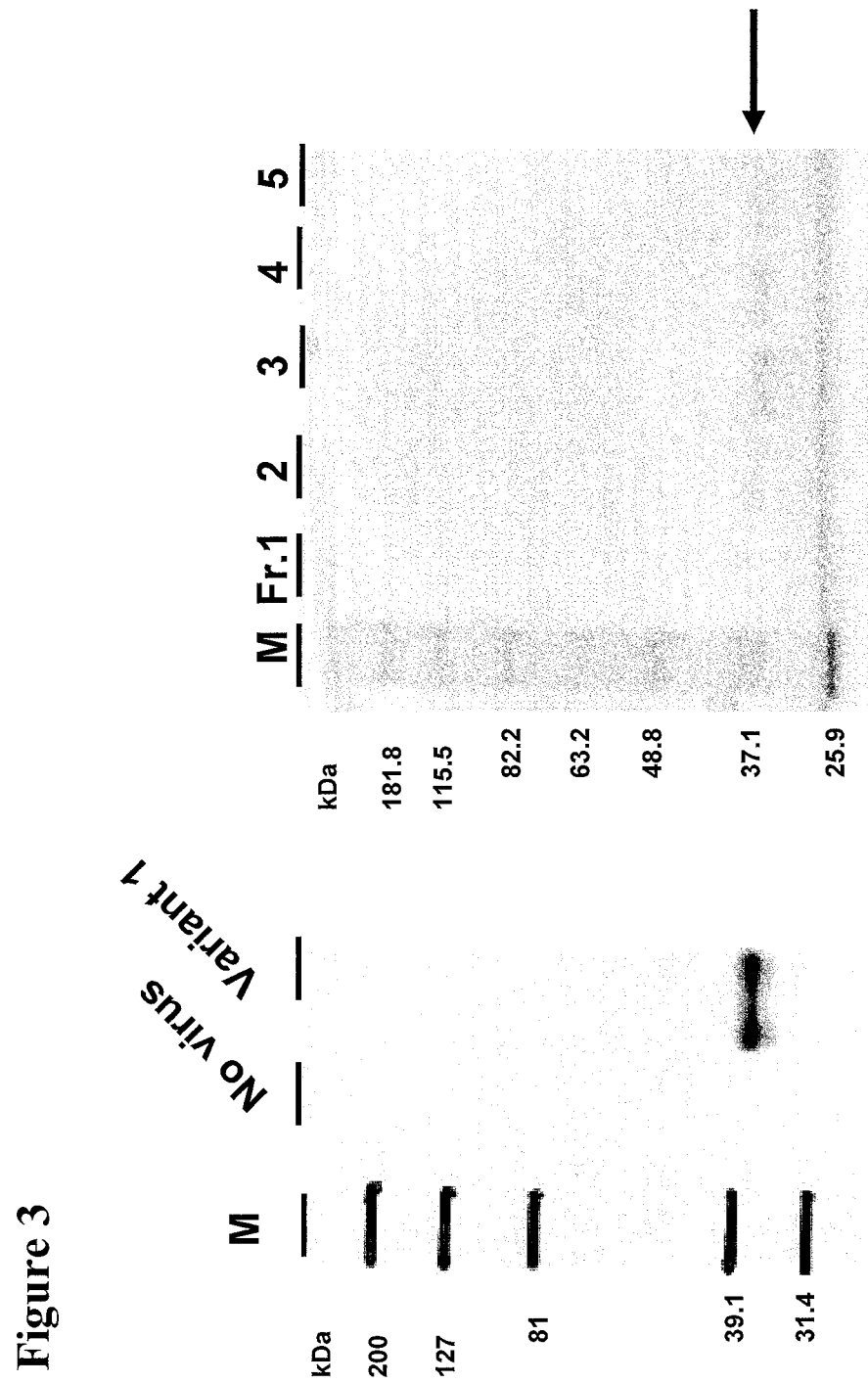
FIG. 3 Expression and purification of Variant 1 with baculovirus

Purification of a protein of this invention with FLAG was performed by adding a lysate solution to anti-FLAG M2 affinity gel column (Sigma) which was equilibrated with TBS including 0.1% NP-40, washing with the same solution, eluting with an eluate (Gly-HCl including 0.1% NP-40, pH 3.5) (1 ml/fraction) and neutralizing with 1 M Tris-HCl, pH 8.0 (20 µl per 1 ml of the eluate) without delay. By Western blotting of purification fraction or dyeing by Bio-Safe Coomassie (Bio-Rad) after SDS-PAGE, about 37 kDa band was confirmed (FIG. 3). After SDS-PAGE and transferring on PVDF membrane (BIO-RAD), a partial amino acid sequence of peptide fragment that this band was dissolved and digested by BLase was analyzed by an amino acid sequencer. Because it corresponded to an amino acid sequence comprising SEQ ID: 2, it was confirmed that this protein was a protein of this invention.

EXAMPLE 3

Angiogenesis Inhibiting Effect of a Protein of this Invention In Vivo

Figure 4:
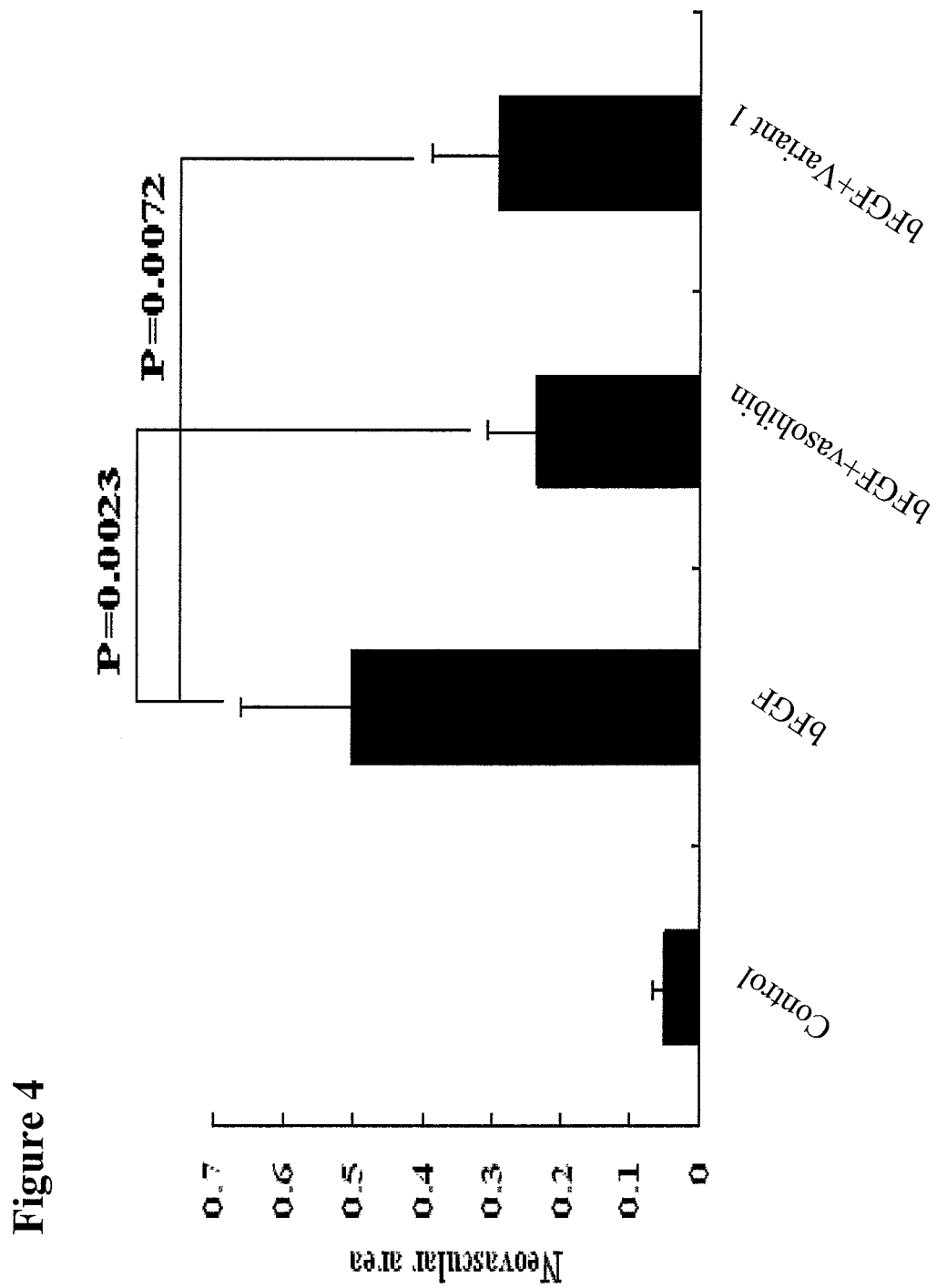
FIG. 4 In vivo inhibiting effect of Variant 1 on angiogenesis

Whether a protein of this invention has angiogenesis inhibitory ability as Vasohibin or not was examined by a mouse cornea micropocket assay according to a method described in J. Immunol. 170: 5704-5711, (2003) and FASAB J. 18: 300-310, (2004). 80 ng FGF-2 protein (fibroblast growth factor-2, BD Biosciences) was mixed to 0.3 µg hydron reagent (IFN Sciences), 5 ng Vasohibin or a protein of this invention was added thereto and the mixture was transplanted to cornea of a BALB/c male mouse. After 7 days, angiogenesis elongated to cornea was took photos and quantitative analysis of angiogenesis was performed with image analysis software, National Institutes of Health (NIH) image. As a result, angiogenesis induced by FGF-2 was significantly inhibited under the presence of a protein of this invention and this effect turned out to be approximate equivalent to inhibition of angiogenesis by Vasohibin (FIG. 4).

EXAMPLE 4

A Method for Screening a Low Molecular Weight Compound Inducing Expression of a Protein of this Invention PC-3 cells which are human prostatic cancer cell strain is plated in DMEM medium including 10% calf serum of 96-well plate on the market (for example, 96 Well Cell Culture Cluster made by Costar) with $1.5-2.0\times10^4$ cells/well (100 µl/well) and incubated standing overnight. The medium is replaced with 100 ml DMEM medium without calf serum, added respectively 1-5 µl of a low-molecular weight compound dissolved in 10% DMSO (The final concentration is 1-5 mg/ml) and incubated standing for more 20 hours. As a control, 10% DMSO without a compound is used. After the reaction, culture supernatant is collected and amount of a protein of this invention in the supernatant is measured by ELISA to confirm presence or absence of induction of expression. ELISA is carried out by adding 50 µl collected culture supernatant and 50 µl assay buffer (for example, 100 mM PBS solution including 0.5% BSA) to an immunoplate immobilized antibodies against a protein of this invention (for example, Immunomodule made by Nunc), and reacting at 4° C. overnight. After washing with a washing solution (for example, physiological saline solution including 0.05% Tween 20) at 3 times, 100 µl antibodies recognized the other part of a protein of this invention and labeled with horseradish peroxidase (HRP) is added thereto with concentration of 1 µg/ml and the mixture is standing at room temperature for 3 hours. After washing with a washing solution at 3 times, 100 µl TMB solution which is a color reagent is added thereto, and the mixture is reacted at room temperature for 30 minutes. After the reaction, 100 µl of 0.18N sulphuric acid solution is added thereto to stop the reaction. The absorbancy at 450 nm is measured and the amount of the protein of this invention in the supernatant is calculated with absorbancy of recombinant of a protein of this invention measured at the same time. A low-molecular weight compound added in a sample which is detected the larger amount of a protein of this invention compared to a control added only 10% DMSO is decided as a candidate compound of an angiogenesis inhibitor.

Industrial Applicability

A protein of this invention, the gene or the like can be used as an angiogenesis inhibitor. An antibody against the protein or the like can be used as an angiogenesis promoter. Additionally, an angiogenesis inhibitor or promoter can be screened with the protein, gene, antibody or the like.

Sequence Listing Free Text

SEQ ID: 13 shows a RT-PCR forward primer of AK022567 (SEQ ID: 1).

SEQ ID: 14 shows a RT-PCR reverse primer of AK022567 (SEQ ID: 1).

The invention claimed is:

1. A method for inhibiting angiogenesis comprising contacting a tissue with an expression vector comprising a polynucleotide having the nucleotide sequence consisting of SEQ ID NO: 1 or having a nucleotide sequence that is at least 80% identical to the sequence of SEQ ID NO: 1, and optionally comprising a second polynucleotide encoding a secretory signal sequence operably linked to said polynucleotide, or contacting a tissue with a cell that comprises said expression vector.

2. The method for inhibiting angiogenesis of claim 1, wherein the expression vector comprises a polynucleotide having a nucleotide sequence that is at least 90% identical to the sequence of SEQ ID NO: 1, and optionally comprises a second polynucleotide encoding a secretory signal sequence operably linked to said polynucleotide.

* * * * *

SEQUENCE LISTING

```
<160> NUMBER OF SEQ ID NOS: 14

<210> SEQ ID NO 1
<211> LENGTH: 2701
<212> TYPE: DNA
<213> ORGANISM: Homo sapiens
<300> PUBLICATION INFORMATION:
<308> DATABASE ACCESSION NUMBER: NCBI/AK022567
<309> DATABASE ENTRY DATE: 2000-08-23

<400> SEQUENCE: 1
attcgagaat gggacatgga atgaggcgac ggccccagca agcccagca gccccagccc      60 cagccccagg cccagcagca gcagcagcag cccctgctct cccgccgccc ggagaggctc     120
tgcagccatg aagccaaccg tcccgaggca ccgccggtaa gcagggagcc tccgcggagc     180
```

```
tcccgccgcc gctccccctt ggcgccaaag gcacccggtc ccggagcagc cacgcgcggc        240
ccgtgagcct cgccaccagc gggggctcag aggaggagga caaagacggc ggggtgctgt        300
tccacgtcaa caagagcggc ttccccatcg acagccacac ctgggagcgc atgtggatgc        360
acgtggccaa ggtgcaccct aagggggag aaatggtggg cgccatcagg aacgccgcct         420
tcttggcaaa gccttcaata ccccaggtcc caaactacag gctgtcgatg acgatcccag        480
actggctcca ggcgatccag aattacatga agaccctaca atataatcac acagggaccc       540
agttctttga aattaggaaa atgagaccgc tgagtgggtt aatggaaaca gcaaaagaaa       600
tgacccgaga gtccttgcct atcaaatgcc ttgaagctgt catcctgggc atctacttaa      660
ccaatgggca gccttccatt gagcggttcc ccatcagctt aaaacctac ttctcaggaa       720 actactttca ccacgttgtg ctgggatttt actgcaatgg ccgctatggc tcattgggca     780
tgagccgcag ggctgagctg atggacaagc cattgactt tcggactctg agtgacctca      840
tctttgactt tgaggactct tacaagaaat acctgcacac agtcaagaag gtcaagattg    900
ggctgtacgt cccccatgag cctcatagct ccagcccat tgagtggaag cagctggtcc    960
tcaacgtctc aaagatgctg agggctgaca taaggaagga gctggagaaa tatgccaggg  1020
acatgagaat gaagatcctg aaacctgcaa gtgcccactc tccgacccaa gtgagaagcc  1080
ggggaaaatc cctgtccccc agaaggagac aggcaagccc cccgaggagg ctcggccggc  1140
gagagaagtc gcctgcactg cctgaaaaga aggtggctga tctgagcact ctgaatgaag  1200
tgggctatca aatccgaatt tagccaagcc ataccggcca gcaagagggt ttctgtggtg  1260
cttctctctg cactttaccc agcatcttca ggaggaactg caactattta ttaagaactt  1320
gtgaatttta tttttaagga ttcacctgga aatagaatct gagtgggtgg taaccattag  1380
ctttaaaaaa ttcactaaaa ggcaccatga aaaggctgaa gtaataagcc ccactggggt  1440
tggactatgt ccctcactca agatcttaag gataaccgta actgaagttt tatattttc   1500 catttaccta cttttctttta cttgctttga acattatgcc tcaccaatag taaatgttca  1560
tgaaataatc tcttgaactt ttggtatagt aaggtaactc taacagtatt actgtctttt  1620
tcagcaataa cagaaagcaa aaatgggtgg gtttttttta agcagttatt acctcagcat  1680
tttgacatca gatatgcaaa cttaatggcg ttttgttttt ttatattcta tttgtattct  1740
ttccccagta tttcccatgg ggatctccac aagtttggag ttttttcctg gtgcacacac  1800
gtgaggagat ttaaggtact atatgcaagt gttttactaa aaagcactga aattcttctg  1860
gcaatacaag aaccattttc aggatcttgg agttacttcc ttcttaatct ttcttaaagc  1920
attcactgat gttttttgttt tttcaaaatg aaacaaaaat atcacattga aagctagtc   1980 tatgttctgt cactaacatt taaactttgc agactctaac aaaaagcaca agaggtcacg   2040
tactattata caaatttagc ggtactggat ttacctctga cattaacaca ctcaggcaga   2100
gaccaggagt gatcagcagg tcttcagaac caaaaaacct ttctgttcac atttcatctg   2160 attttttaaac tgaggcaggc tttgattctt ctgaaggatg ccaagaatca aactaaggga   2220
ggactcactg ttaaagatgt gttctgatgt cttatattaa gaccaaatgt gacatgatgt   2280
gattatcttc cagtactttg cttttaggta ccatttcatg acattttagg aatgagtatt   2340
ggaaaatata agaattaga aaagcagcac tttttttta atggaaaagt cttcggtcca    2400
gtgttacacc ttatagtgta attcagtccc taagcacaga atgaatgtct ggcctgcata   2460
tggtagttac agtgtaacct ctggctgcag accacacagg acaaccctaa cagcctagtc   2520
ttgtatggtg taaatatcaa gagtacagct tcaatttcat ttgctttatc ttagcaacaa   2580
```

```
tgccaactca ggagagcaga cggccgattt cagtgaagtc tggtagtcaa cagatgttat    2640
ttcagtctca gtgcatctcc tctggctttc tttgactgaa ggtgtttata ggaaggaagt    2700
t                                                                     2701
```

<210> SEQ ID NO 2
<211> LENGTH: 290
<212> TYPE: PRT
<213> ORGANISM: Homo sapiens
<300> PUBLICATION INFORMATION:
<308> DATABASE ACCESSION NUMBER: NCBI/BAB14103
<309> DATABASE ENTRY DATE: 2000-08-23

<400> SEQUENCE: 2

```
Met Trp Met His Val Ala Lys Val His Pro Lys Gly Gly Glu Met Val
1               5                   10                  15

Gly Ala Ile Arg Asn Ala Ala Phe Leu Ala Lys Pro Ser Ile Pro Gln
            20                  25                  30

Val Pro Asn Tyr Arg Leu Ser Met Thr Ile Pro Asp Trp Leu Gln Ala
        35                  40                  45

Ile Gln Asn Tyr Met Lys Thr Leu Gln Tyr Asn His Thr Gly Thr Gln
    50                  55                  60

Phe Phe Glu Ile Arg Lys Met Arg Pro Leu Ser Gly Leu Met Glu Thr
65                  70                  75                  80

Ala Lys Glu Met Thr Arg Glu Ser Leu Pro Ile Lys Cys Leu Glu Ala
                85                  90                  95

Val Ile Leu Gly Ile Tyr Leu Thr Asn Gly Gln Pro Ser Ile Glu Arg
            100                 105                 110

Phe Pro Ile Ser Phe Lys Thr Tyr Phe Ser Gly Asn Tyr Phe His His
        115                 120                 125

Val Val Leu Gly Ile Tyr Cys Asn Gly Arg Tyr Gly Ser Leu Gly Met
    130                 135                 140

Ser Arg Arg Ala Glu Leu Met Asp Lys Pro Leu Thr Phe Arg Thr Leu
145                 150                 155                 160

Ser Asp Leu Ile Phe Asp Phe Glu Asp Ser Tyr Lys Lys Tyr Leu His
                165                 170                 175

Thr Val Lys Lys Val Lys Ile Gly Leu Tyr Val Pro His Glu Pro His
            180                 185                 190

Ser Phe Gln Pro Ile Glu Trp Lys Gln Leu Val Leu Asn Val Ser Lys
        195                 200                 205

Met Leu Arg Ala Asp Ile Arg Lys Glu Leu Glu Lys Tyr Ala Arg Asp
    210                 215                 220

Met Arg Met Lys Ile Leu Lys Pro Ala Ser Ala His Ser Pro Thr Gln
225                 230                 235                 240

Val Arg Ser Arg Gly Lys Ser Leu Ser Pro Arg Arg Gln Ala Ser
                245                 250                 255

Pro Pro Arg Arg Leu Gly Arg Arg Glu Lys Ser Pro Ala Leu Pro Glu
            260                 265                 270

Lys Lys Val Ala Asp Leu Ser Thr Leu Asn Glu Val Gly Tyr Gln Ile
        275                 280                 285

Arg Ile
    290
```

<210> SEQ ID NO 3
<211> LENGTH: 3580
<212> TYPE: DNA
<213> ORGANISM: Homo sapiens

```
<300> PUBLICATION INFORMATION:
<308> DATABASE ACCESSION NUMBER: NCBI/BC051856
<309> DATABASE ENTRY DATE: 2003-03-01

<400> SEQUENCE: 3
gccccagcag ccccagcccc agcccaggc  ccagcagcag cagcagcagc ccctgctctc      60
ccgccgcccg gagaggctct gcagccatga agccaaccgt cccgaggcac cgccggtaag     120
cagggagcct ccgcggagct cccgccgccg ctccccttg  gtgagtcctg ccgcagcgag     180
aggcatggag aaggccgccc ccgcggggcg ctgatcccct cgccgcgccc gcgcgcacac     240
gccccccgcc gccgccgccg ctgccgccgc cgcgcgcccc cagtacctcg ctccccaccc     300
aggccccacc atgaccggct ccgcggccga cactcaccgc tgccccacc  ccaaaggcgc     360 caaaggcacc cggtcccgga gcagccacgc gcggcccgtg agcctcgcca ccagcggggg     420
ctcagaggag gaggacaaag acggcggggt gctgttccac gtcaacaaga gcggcttccc     480
catcgacagc cacacctggg agcgcatgtg gatgcacgtg gccaaggtgc accctaaggg     540
gggagaaatg gtgggcgcca tcaggaacgc cgccttcttg gcaaagcctt caataccccca   600 ggtcccaaac tacaggctgt cgatgacgat cccagactgg ctccaggcga tccagaatta    660
catgaagacc ctacactact taaccaatgg gcagccttcc attgagcggt tccccatcag    720 cttttaaaacc tacttctcag gaaactactt tcaccacgtt gtgctgggga tttactgcaa   780
tggccgctat ggctcattgg gcatgagccg cagggctgag ctgatggaca agccattgac    840
ttttcggact ctgagtgacc tcatctttga ctttgaggac tcttacaaga atacctgca    900 cacagtcaag aaggtcaaga ttgggctgta cgtcccccat gagcctcata gcttccagcc    960
cattgagtgg aagcagctgg tcctcaacgt ctcaaagatg ctgagggctg acataaggaa   1020
ggagctggag aaatatgcca gggacatgag aatgaagatc ctgaaacctg caagtgccca   1080
ctctccgacc caagtgagaa gccggggaaa atccctgtcc cccagaagga cacaggcaag   1140
ccccccgagg aggctcggcc ggcgagagaa gtcgcctgca ctgcctgaaa agaaggtggc   1200
tgatctgagc actctgaatg aagtgggcta tcaaatccga atttagccaa gccataccgg   1260
ccagcaagag ggtttctgtg gtgcttctct ctgcacttta cccagcatct tcaggaggaa   1320
ctgcaactat ttattaagaa cttgtgaatt ttattttaa  ggattcacct ggaaatagaa   1380
tctgagtggg tggtaaccat tagctttaaa aaattcacta aaaggcacca tgaaaaggct   1440
gaagtaataa gccccactgg ggttgaacta tgtccctcac tcaagatctt aaggataacc   1500
gtaactgaag ttttatattt ttccatttac ctactttctt ttacttgctt tgaacattat   1560
gcctcaccaa tagtaaatgt tcatgaaata atctcttgaa cttttggtat agtaaggtaa   1620
ctctaacagt attactgtct ttttcagcaa taacagaaag caaaaatggg tgggttttt    1680 ttaagcagtt attacctcag cattttgaca tcagatatgc aaacttaatg gcgttttgtt   1740
tttttatatt ctatttgtat tctttcccca gtatttccca tggggatctc acaagtttg    1800 gagttttttc ctggtgcaca cacgtgagga gatttaaggt actatatgca agtgttttac   1860
taaaaagcac tgaaattctt ctggcaatac aagaaccatt tcaggatct  tggagttact   1920 tccttcttaa tctttcttaa agcattcact gatgtttttg tttttcaaa  atgaaacaaa   1980 aatatcacat tgagaagcta gtctatgttc tgtcactaac atttaaactt tgcagactct   2040
aacaaaaagc acaagaggtc acgtactatt atacaaattt agcggtactg gatttacctc   2100
tgacattaac acactcaggc agagaccagg agtgatcagc aggtcttcag aaccaaaaaa   2160
cctttctgtt cacatttcat ctgattttta aactgaggca ggctttgatt cttctgaagg   2220
```

```
atgccaagaa tcaaactaag ggaggactca ctgttaaaga tgtgttctga tgtcttatat    2280
taagaccaaa tgtgacatga tgtgattatc ttccagtact ttgcttttag gtaccatttc    2340
atgacatttt aggaatgagt attggaaaat ataagaatt agaaaagcag cactttttt     2400 ttaatggaaa agtcttcggt ccagtgttac accttatagt gtaattcagt ccctaagcac    2460
agaatgaatg tctggcctgc atatggtagt tacagtgtaa cctctggctg cagaccacac    2520 aggcaaccc taacagccta gtcttgtatg gtgtaaatat caagagtaca gcttcaattt     2580
catttgcttt atcttagcaa caatgccaac tcaggagagc agacggccga tttcagtgaa    2640
gtctggtagt caacagatgt tatttcagtc tcagtgcatc tcctctggct ttctttgact    2700
gaaggtgttt ataggaagga agttaaaaaa aaaaaagctc attgagattc tttaccaatt    2760
ctttacaaga tttctggggg tgacaggaa agcaaaagga cttcaaagca aagggtgca     2820 caagagctta cttcaccctg aaaatcagta ttattaatga aaagtactgt tttcttaaag    2880
aagtcgaatg tcctttagat gaacaagacc aagtatacat ctccattaga ttaaaatgta    2940
gcacagggtt aaaaattatc agtttaatct ctttaagaac agtattatca gagtttaaaa    3000
tgagttagct ctgtttatct acacacagca aacccattcg cagcctcttg cccacatgta    3060
ttcagatgtt tgaaatagtg aatcatttca ttttcattct aaaacaatac tgacttagcc    3120
atataccttc tgtttgtcaa tctgaaactt gcttacatct aataagtaga cctcttataa    3180
cactgcaacc attctaagag ttggaattta ttttgccaa gtattaagta ctgttacatc     3240
taaaatacag aatgtcaaat ggttgcatag cttgtttccc acaacaagga ggaaaagaac    3300
aggaatacaa actctgtaat atgctgataa agaagcctta gaactgccaa ctggcttgat    3360
ggttcaatta gtaagctaat ttctcccaca cccgctcctt gattttttaga ctaattttcc    3420 caaagcaagg tttagtcaca caaacttgaa agtcactta aaatgttctt agttgtcatc     3480
ctacttttat tgcctatgga atatgctaat ttctaaaaaa aatacgggag aggcaccaaa    3540
cccctaaatt ctagtgcaat aatttaaaaa aaaaaaaaaa                          3580
```

<210> SEQ ID NO 4
<211> LENGTH: 311
<212> TYPE: PRT
<213> ORGANISM: Homo sapiens
<300> PUBLICATION INFORMATION:
<308> DATABASE ACCESSION NUMBER: NCBI/AAH51856
<309> DATABASE ENTRY DATE: 2003-05-01

<400> SEQUENCE: 4

```
Met Thr Gly Ser Ala Ala Asp Thr His Arg Cys Pro His Pro Lys Gly
1               5                   10                  15

Ala Lys Gly Thr Arg Ser Arg Ser Ser His Ala Arg Pro Val Ser Leu
            20                  25                  30

Ala Thr Ser Gly Gly Ser Glu Glu Asp Lys Asp Gly Gly Val Leu
        35                  40                  45

Phe His Val Asn Lys Ser Gly Phe Pro Ile Asp Ser His Thr Trp Glu
    50                  55                  60

Arg Met Trp Met His Val Ala Lys Val His Pro Lys Gly Gly Glu Met
65                  70                  75                  80

Val Gly Ala Ile Arg Asn Ala Ala Phe Leu Ala Lys Pro Ser Ile Pro
                85                  90                  95

Gln Val Pro Asn Tyr Arg Leu Ser Met Thr Ile Pro Asp Trp Leu Gln
            100                 105                 110

Ala Ile Gln Asn Tyr Met Lys Thr Leu His Tyr Leu Thr Asn Gly Gln
        115                 120                 125
```

```
Pro Ser Ile Glu Arg Phe Pro Ile Ser Phe Lys Thr Tyr Phe Ser Gly
    130                 135                 140

Asn Tyr Phe His His Val Val Leu Gly Ile Tyr Cys Asn Gly Arg Tyr
145                 150                 155                 160

Gly Ser Leu Gly Met Ser Arg Arg Ala Glu Leu Met Asp Lys Pro Leu
                165                 170                 175

Thr Phe Arg Thr Leu Ser Asp Leu Ile Phe Asp Phe Glu Asp Ser Tyr
                180                 185                 190

Lys Lys Tyr Leu His Thr Val Lys Val Lys Ile Gly Leu Tyr Val
            195                 200                 205

Pro His Glu Pro His Ser Phe Gln Pro Ile Glu Trp Lys Gln Leu Val
    210                 215                 220

Leu Asn Val Ser Lys Met Leu Arg Ala Asp Ile Arg Lys Glu Leu Glu
225                 230                 235                 240

Lys Tyr Ala Arg Asp Met Arg Met Lys Ile Leu Lys Pro Ala Ser Ala
                245                 250                 255

His Ser Pro Thr Gln Val Arg Ser Arg Gly Lys Ser Leu Ser Pro Arg
                260                 265                 270

Arg Arg Gln Ala Ser Pro Pro Arg Leu Gly Arg Glu Lys Ser
            275                 280                 285

Pro Ala Leu Pro Glu Lys Lys Val Ala Asp Leu Ser Thr Leu Asn Glu
    290                 295                 300

Val Gly Tyr Gln Ile Arg Ile
305                 310

<210> SEQ ID NO 5
<211> LENGTH: 3291
<212> TYPE: DNA
<213> ORGANISM: Homo sapiens
<300> PUBLICATION INFORMATION:
<308> DATABASE ACCESSION NUMBER: NCBI/BC053836
<309> DATABASE ENTRY DATE: 2003-06-13

<400> SEQUENCE: 5
ggcgacggcc ccagcaagcc ccagcagccc cagccccagc cccaggccca gcagcagcag      60
cagcagcccc tgctctcccg ccgcccggag aggctctgca gccatgaagc caaccgtccc     120
gaggcaccgc cgtaagcagg gagcctccgc ggagctcccg ccgccgctcc ccttggtga     180 gtcctgccgc agcgagaggc atggagaagg ccgcccccgc ggggcgctga tcccctcgcc     240
gcgcccgcgc gcacacgccc ccgccgccg cgccgctgc cgccgccgcg cgccccagt     300 acctcgctcc ccgcccaggc ccaccatga ccggctccgc ggccgacact caccgctgcc     360
cccaccccaa aggcgccaaa ggcacccggt cccggagcag ccacgcgcgg cccgtgagcc     420
tcgccaccag cggggggctca gaggaggagg acaaagacgg cggggtgctg ttccacgtca     480
acaagagcgg cttcccccatc gacagccaca cctgggagcg catgtggatg cacgtggcca     540
aggtgcaccc taaggggga gaaatggtgg cgccatcag gaacgccgcc ttcttggcaa     600
agccttcaat accccaggtc ccaaactaca ggctgtcgat gacgatccca gactggctcc     660
aggcgatcca gaattacatg aagaccctac aatataatca cagggacc cagttctttg     720 aaattaggaa aatgagaccg ctgagtgggt aatggaaac agcaaaagaa atgacccgag     780
agtccttgcc tatcaaatgc cttgaagctg tcatcctggg cataacccac agctaaaaca     840
agggtctagc ttctcccaca ctttctgttc cattttcac cagactcccg gctcttcagc     900
ctgagaggaa tatggtgcag agaaactgtg atggcatcga catattggtg gtgatgacca     960
```

```
cctcccttac acaatagtct catccctgca caattttata cattcgagca tcatgccatt    1020
ggaatcaccc acaaccttt  gaaattgtgg ggatagaccc aggaacagcc tttgagcctg    1080
atctgccaca atcagataga agagcaaaga tgctccgaag tcctatggga tggatggctg    1140
taagggacag tggaaaagga aacactgcaa gacaggagct tgagagatgg tcccaggcaa    1200
gatcagttag gtccttgagc gctgtgctga gaaatgactt ttttccaaaa ggcaatgggc    1260
aacccagatg aaagctctga agcagaggtg tggcatgctt aggtatatgc tctagagagg    1320
tagttctcca aagcacaggc tgaaggacag attgggaaag gctgggctgg atcagcaaag    1380
cccgttggga gctgttacat gagggaatgg tgaggctaga ctcatggccc tggggatggg    1440
aatggatttc agggaatggt tttaagagct atcaaggaga tagaatgtat aggacttgca    1500
ggccaaccag acgcaggagt taatgaggaa ggagtcaacg tctccaggtt tctgaattgg    1560
gcaatcgact gcgggattag ctggaggaat gagagtggca gagaaaggat atgcgtcaat    1620
gcagacctga actaagacag tgccagtgaa ggtggaggga agggatggag gcatacatca    1680
tcaccaccac taggggactg cttagatggg aggagttatt ggagaaaggc agtgactcca    1740
catttctggc ttgcatgata atgccacaag ggaagaactt caaggagagg atcggattta    1800
gggaaagatg agctcagatt tggacatgtg aaatttgagg tgccttgtgg gatgtcggaa    1860
tgaggtattt gcaatgtgga gctcacaggg gaatctgcac tggaaatgcg aatttaggag    1920
ctgtgattag gaggttgtgc ttactgttca ataagtgaaa ggagaaaaag atcaaagatg    1980
aaatcagtat ttttggtct  agtttggcac aaagagccca tgaaagagac ttaagaagga    2040
aagagaggta gaaagaaaac caggagagaa agggatgga  gaggtcagtg gaaggacatg    2100
tggctcagaa ttagactggg gacaggagga ttggtctagt ctgttttctg ggtctcctgg    2160
acatctttgt gggaaggaga atctctgtgc ctctctgcag tctgtggaac acttgcagcc    2220
ctgatctgaa accagattga ccacaggtgc cttggctgac atttgaaaaa tggaaacttg    2280
aaccttactg aggcccctcc ccaaccctct tgtcatcctc ctccctgttt cccacaaagg    2340
agatgaaaca tgtgcctggg gaacccagca ggaagctggg aatggggtc  ggggcagcag    2400
atggctcagg gcccaactc  tttagtggca ggagtcagcc acagctgttc agcgaagcct    2460
cctgcaagtt taatgggggc agatgattgg ctggggattt gctggtggaa gagatcaacg    2520
aaggggaaca caagcccagg cccttcatgg ggtagacaag ctaacttcag actctttgtt    2580
gaggggtgtc tgagtgcctc tggatttagg tcattgaaat gaccacctcc cttacacaat    2640
agtctcatcc ctgcacaatt ttatacattt gcgcatcatg ccactggaat cacccacgac    2700
cttttggaat tgtggggata gacccaggaa cagcctttga gcctgtccaa atcagagaca    2760
gtgtgctcgt ggttttcctt tgttcttatc cttctgacat ttcagaaaag tgcaggaagg    2820
tggagagctt cagttcacgc tgctgaactc agggaaattt gactcttgca cacagacagg    2880
aaacacagat ccgaattctt cttctttttt tttttttttg agacggagtc ttggtctgtc    2940
gcaccactgc actccagcct gggtgacaga gtgagactgt gtctcaaaaa aatgaaaaaa    3000
aaaaaaaaga ccaccattcc tccccagaaa tgaaacccca tacccgttaa aaagtactcc    3060
ccatttcccc cctccagccc ctgcccacca ccgttctact ctctgtctgt atgcacttgc    3120
tactccaggt accgcagatg agtggaatca taccatattt gtcctttgt  attaggctga    3180
tttcactcag catgtcttca aggctcattc tgcacattgc agaatttccc tcccttatga    3240
ggctgaataa attctattac atgtatacac taaaaaaaaa aaaaaaaaa  a             3291
```

<210> SEQ ID NO 6

<211> LENGTH: 169
<212> TYPE: PRT
<213> ORGANISM: Homo sapiens
<300> PUBLICATION INFORMATION:
<308> DATABASE ACCESSION NUMBER: NCBI/AAH53836
<309> DATABASE ENTRY DATE: 2003-06-13

<400> SEQUENCE: 6

Met Thr Gly Ser Ala Ala Asp Thr His Arg Cys Pro His Pro Lys Gly
1               5                   10                  15

Ala Lys Gly Thr Arg Ser Arg Ser Ser His Ala Arg Pro Val Ser Leu
            20                  25                  30

Ala Thr Ser Gly Gly Ser Glu Glu Asp Lys Asp Gly Gly Val Leu
        35                  40                  45

Phe His Val Asn Lys Ser Gly Phe Pro Ile Asp Ser His Thr Trp Glu
    50                  55                  60

Arg Met Trp Met His Val Ala Lys Val His Pro Lys Gly Gly Glu Met
65                  70                  75                  80

Val Gly Ala Ile Arg Asn Ala Ala Phe Leu Ala Lys Pro Ser Ile Pro
                85                  90                  95

Gln Val Pro Asn Tyr Arg Leu Ser Met Thr Ile Pro Asp Trp Leu Gln
            100                 105                 110

Ala Ile Gln Asn Tyr Met Lys Thr Leu Gln Tyr Asn His Thr Gly Thr
        115                 120                 125

Gln Phe Phe Glu Ile Arg Lys Met Arg Pro Leu Ser Gly Leu Met Glu
    130                 135                 140

Thr Ala Lys Glu Met Thr Arg Glu Ser Leu Pro Ile Lys Cys Leu Glu
145                 150                 155                 160

Ala Val Ile Leu Gly Ile Thr His Ser
                165

<210> SEQ ID NO 7
<211> LENGTH: 1790
<212> TYPE: DNA
<213> ORGANISM: Homo sapiens
<300> PUBLICATION INFORMATION:
<308> DATABASE ACCESSION NUMBER: NCBI/BC028194
<309> DATABASE ENTRY DATE: 2002-04-08

<400> SEQUENCE: 7
gcagccccag cccagccc aggcccagca gcagcagcag cagcccctgc tctcccgccg      60
cccggagagg ctctgcagcc atgaagccaa ccgtcccgag ccttcaatac cccaggtccc    120
aaactacagg ctgtcgatga cgatcccaga ctggctccag gcgatccaga attacatgaa    180
gaccctacag tatccttcca accaaggtct gagcacaccc agccagggga caggcatggt    240
gatcgcaagc ctggtggcaa atctgtcccc agctggtcat caaaagctct ctaaggttaa    300
tggaaacagc aaaagaaatg acccgagagt ccttgcctat caaatgcctt gaagctgtca    360
tcctgggcat ctacttaacc aatgggcagc cttccattga gcggttcccc atcagcttta    420
aaacctactt ctcaggaaac tactttcacc acgttgtgct ggggatttac tgcaatggcc    480
gctatggctc attgggcatg agccgcaggg ctgagctgat ggacaagcca ttgacttttc    540
ggactctgag tgacctcatc tttgactttg aggactctta caagaaatac ctgcacacag    600
tcaagaaggt caagattggg ctgtacgtcc ccatgagcc tcatagcttc agcccattg     660 agtggaagca gctggtcctc aacgtctcaa agatgctgag ggctgacata aggaaggagc    720
tggagaaata tgccagggac atgagaatga agggcttgtg cagtcactaa gagaaaagga    780
ttatgctgac ttcaggcctg gctatgttta gcacttgtgg acttgtcatc ttcactctgc    840

```
aggacctgga gtggagattc ctgatcaatt aaaaccattc tgtcatatgt gtgggatggg        900
agcatcagag gaagaacagg ctggtttctg aggcaataga gatgggactt tgccttcgtg        960
aggagaggaa cttgccaagc aaacaaacac agccccgggg agactgaggc attgggctgt       1020
gttcctctct ctacacggca cagggagcac aatgtgacca tctgtatatc tgtcttggaa       1080
gtggtgccct tgctgcttga cagtacagga cgagagagga atgtgtgtgt ctccagcctc       1140
cttttttaga agtcttcctg ctcaatgcct tctaaaccat ggcatcatga ttgggctggg       1200
gggtggaatg tggtgctaga agaagacctg agggtggagg tcccttagga accagggtga       1260
ttaactcctc acatctcctt cagatcctga aacctgcaag tgcccactct ccgacccaag       1320
tgagaagccg gggaaaatcc ctgtccccca gaaggagaca ggcaagcccc ccgaggaggc       1380
tcggccggcg agagaagtcc cctgaggcca gtgatcccac atctacttct tagaccaaaa       1440
taacccactt aagcaatgac agattggaga tgctggggat gcccaaattc accagcgata       1500
atccgctggc aaatatttga actatagcca tcctgggaaa aaatactgct tttcttaata       1560
atagcagcat gctgtgtcac ccagcctctt gccatgctgg aaccatgtgg cacagtgcac       1620
agggggcttg gttgaatccc aactgtgcca cgtgttagct gtgcagctgg gcacatcctt       1680
cctcctcggg gagccttggt ttcttcatcc ataaagagt atcaaatgct aaaaaaaaaa         1740
aaaaaaaaaa aaaaaaaaaa aaaaaaaaaa aaaaaaaaa aaaaaaaaaa                   1790
```

<210> SEQ ID NO 8
<211> LENGTH: 156
<212> TYPE: PRT
<213> ORGANISM: Homo sapiens
<300> PUBLICATION INFORMATION:
<308> DATABASE ACCESSION NUMBER: NCBI/AAH28194
<309> DATABASE ENTRY DATE: 2002-04-08

<400> SEQUENCE: 8

```
Met Glu Thr Ala Lys Glu Met Thr Arg Glu Ser Leu Pro Ile Lys Cys
1               5                   10                  15

Leu Glu Ala Val Ile Leu Gly Ile Tyr Leu Thr Asn Gly Gln Pro Ser
            20                  25                  30

Ile Glu Arg Phe Pro Ile Ser Phe Lys Thr Tyr Phe Ser Gly Asn Tyr
        35                  40                  45

Phe His His Val Val Leu Gly Ile Tyr Cys Asn Gly Arg Tyr Gly Ser
    50                  55                  60

Leu Gly Met Ser Arg Arg Ala Glu Leu Met Asp Lys Pro Leu Thr Phe
65                  70                  75                  80

Arg Thr Leu Ser Asp Leu Ile Phe Asp Phe Glu Asp Ser Tyr Lys Lys
                85                  90                  95

Tyr Leu His Thr Val Lys Lys Val Lys Ile Gly Leu Tyr Val Pro His
            100                 105                 110

Glu Pro His Ser Phe Gln Pro Ile Glu Trp Lys Gln Leu Val Leu Asn
        115                 120                 125

Val Ser Lys Met Leu Arg Ala Asp Ile Arg Lys Glu Leu Glu Lys Tyr
    130                 135                 140

Ala Arg Asp Met Arg Met Lys Gly Leu Cys Ser His
145                 150                 155
```

<210> SEQ ID NO 9
<211> LENGTH: 2897
<212> TYPE: DNA
<213> ORGANISM: Homo sapiens -continued

```
<400> SEQUENCE: 9
attcgagaat gggacatgga atgaggcgac ggccccagca agccccagca gccccagccc      60
cagccccagg cccagcagca gcagcagcag cccctgctct cccgccgccc ggagaggctc     120
tgcagccatg aagccaaccg tcccgaggca ccgccggtaa gcagggagcc tccgcggagc     180
tcccgccgcc gctccccctt ggtgagtcct gccgcagcga gaggcatgga gaaggccgcc     240
cccgcggggc gctgatcccc tcgccgcgcc cgcgcgcaca cgcccccgc cgccgccgcc     300 gctgccgccg ccgcgcgccc ccagtacctc gctccccgcc caggccccac catgaccggc     360
tccgcggcca acactcaccg ctgcccccac cccaaaggcg ccaaaggcac ccggtcccgg     420
agcagccacg cgcggcccgt gagcctcgcc accagcgggg gctcagagga ggaggacaaa     480
gacggcgggg tgctgttcca cgtcaacaag agcggcttcc ccatcgacag ccacacctgg     540
gagcgcatgt ggatgcacgt ggccaaggtg caccctaagg ggggagaaat ggtgggcgcc     600
atcaggaacg ccgccttctt ggcaaagcct tcaataccc aggtcccaaa ctacaggctg     660
tcgatgacga tcccagactg gctccaggcg atccagaatt acatgaagac cctacaatat     720
aatcacacag ggacccagtt ctttgaaatt aggaaaatga ccgctgag tgggttaatg     780 gaaacagcaa agaaatgac ccgagagtcc ttgcctatca aatgccttga agctgtcatc     840
ctgggcatct acttaaccaa tgggcagcct tccattgagc ggttccccat cagctttaaa     900
acctacttct caggaaacta cttttcaccac gttgtgctgg ggatttactg caatggccgc     960
tatggctcat tgggcatgag ccgcagggct gagctgatgg acaagccatt gacttttcgg    1020
actctgagtg acctcatctt tgactttgag gactcttaca agaaatacct gcacacagtc    1080
aagaaggtca agattgggct gtacgtcccc catgagcctc atagcttcca gcccattgag    1140
tggaagcagc tggtcctcaa cgtctcaaag atgctgaggg ctgacataag gaaggagctg    1200
gagaaatatg ccagggacat gagaatgaag atcctgaaac ctgcaagtgc ccactctccg    1260
acccaagtga aagccggggg aaaatccctg tcccccagaa ggagacaggc aagcccccg    1320 aggaggctcg gccggcgaga gaagtcgcct gcactgcctg aaaagaaggt ggctgatctg    1380
agcactctga atgaagtggg ctatcaaatc cgaatttagc caagccatac cggccagcaa    1440
gagggtttct gtggtgcttc tctctgcact ttacccagca tcttcaggag gaactgcaac    1500
tatttattaa gaacttgtga atttatttt taaggattca cctggaaata gaatctgagt    1560
gggtggtaac cattagcttt aaaaaattca ctaaaaggca ccatgaaaag gctgaagtaa    1620
taagccccac tggggttgga ctatgtccct cactcaagat cttaaggata accgtaactg    1680
aagttttata ttttttccatt tacctacttt cttttacttg ctttgaacat tatgcctcac    1740
caatagtaaa tgttcatgaa ataatctctt gaacttttgg tatagtaagg taactctaac    1800
agtattactg tcttttttcag caataacaga aagcaaaaat gggtgggttt tttttaagca    1860
gttattacct cagcattttg acatcagata tgcaaactta atggcgtttt gtttttttat    1920
attctatttg tattctttcc ccagtatttc ccatggggat ctccacaagt ttggagtttt    1980
ttcctggtgc acacacgtga ggagatttaa ggtactatat gcaagtgttt tactaaaaag    2040
cactgaaatt cttctggcaa tacaagaacc attttcagga tcttggagtt acttccttct    2100
taatctttct taaagcattc actgatgttt ttgttttttc aaaatgaaac aaaaatatca    2160
cattgagaag ctagtctatg ttctgtcact aacatttaaa ctttgcagac tctaacaaaa    2220
agcacaagag gtcacgtact attatacaaa tttagcggta ctggatttac ctctgacatt    2280
aacacactca ggcagagacc aggagtgatc agcaggtctt cagaaccaaa aaacctttct    2340
```

```
gttcacattt catctgattt ttaaactgag gcaggctttg attcttctga aggatgccaa      2400
gaatcaaact aagggaggac tcactgttaa agatgtgttc tgatgtctta tattaagacc      2460
aaatgtgaca tgatgtgatt atcttccagt actttgcttt taggtaccat ttcatgacat      2520
tttaggaatg agtattggaa aatataaaga attagaaaag cagcactttt tttttaatgg      2580
aaaagtcttc ggtccagtgt tacaccttat agtgtaattc agtccctaag cacagaatga      2640
atgtctggcc tgcatatggt agttacagtg taacctctgg ctgcagacca cacaggacaa      2700
ccctaacagc ctagtcttgt atggtgtaaa tatcaagagt acagcttcaa tttcatttgc      2760
tttatcttag caacaatgcc aactcaggag agcagacggc cgatttcagt gaagtctggt      2820
agtcaacaga tgttatttca gtctcagtgc atctcctctg gctttctttg actgaaggtg      2880
tttataggaa ggaagtt                                                     2897

<210> SEQ ID NO 10
<211> LENGTH: 355
<212> TYPE: PRT
<213> ORGANISM: Homo sapiens

<400> SEQUENCE: 10

Met Thr Gly Ser Ala Ala Asp Thr His Arg Cys Pro His Pro Lys Gly
1               5                   10                  15

Ala Lys Gly Thr Arg Ser Arg Ser Ser His Ala Arg Pro Val Ser Leu
            20                  25                  30

Ala Thr Ser Gly Gly Ser Glu Glu Asp Lys Asp Gly Gly Val Leu
        35                  40                  45

Phe His Val Asn Lys Ser Gly Phe Pro Ile Asp Ser His Thr Trp Glu
    50                  55                  60

Arg Met Trp Met His Val Ala Lys Val His Pro Lys Gly Gly Glu Met
65                  70                  75                  80

Val Gly Ala Ile Arg Asn Ala Ala Phe Leu Ala Lys Pro Ser Ile Pro
                85                  90                  95

Gln Val Pro Asn Tyr Arg Leu Ser Met Thr Ile Pro Asp Trp Leu Gln
            100                 105                 110

Ala Ile Gln Asn Tyr Met Lys Thr Leu Gln Tyr Asn His Thr Gly Thr
        115                 120                 125

Gln Phe Phe Glu Ile Arg Lys Met Arg Pro Leu Ser Gly Leu Met Glu
    130                 135                 140

Thr Ala Lys Glu Met Thr Arg Glu Ser Leu Pro Ile Lys Cys Leu Glu
145                 150                 155                 160

Ala Val Ile Leu Gly Ile Tyr Leu Thr Asn Gly Gln Pro Ser Ile Glu
                165                 170                 175

Arg Phe Pro Ile Ser Phe Lys Thr Tyr Phe Ser Gly Asn Tyr Phe His
            180                 185                 190

His Val Val Leu Gly Ile Tyr Cys Asn Gly Arg Tyr Gly Ser Leu Gly
        195                 200                 205

Met Ser Arg Arg Ala Glu Leu Met Asp Lys Pro Leu Thr Phe Arg Thr
    210                 215                 220

Leu Ser Asp Leu Ile Phe Asp Phe Glu Asp Ser Tyr Lys Lys Tyr Leu
225                 230                 235                 240

His Thr Val Lys Lys Val Lys Ile Gly Leu Tyr Val Pro His Glu Pro
                245                 250                 255

His Ser Phe Gln Pro Ile Glu Trp Lys Gln Leu Val Leu Asn Val Ser
            260                 265                 270

Lys Met Leu Arg Ala Asp Ile Arg Lys Glu Leu Glu Lys Tyr Ala Arg
```

```
            275                 280                 285
Asp Met Arg Met Lys Ile Leu Lys Pro Ala Ser Ala His Ser Pro Thr
    290                 295                 300

Gln Val Arg Ser Arg Gly Lys Ser Leu Ser Pro Arg Arg Gln Ala
305                 310                 315                 320

Ser Pro Pro Arg Arg Leu Gly Arg Arg Glu Lys Ser Pro Ala Leu Pro
                325                 330                 335

Glu Lys Lys Val Ala Asp Leu Ser Thr Leu Asn Glu Val Gly Tyr Gln
            340                 345                 350

Ile Arg Ile
        355

<210> SEQ ID NO 11
<211> LENGTH: 5747
<212> TYPE: DNA
<213> ORGANISM: Homo sapiens
<300> PUBLICATION INFORMATION:
<308> DATABASE ACCESSION NUMBER: NCBI/NM_014909
<309> DATABASE ENTRY DATE: 2004-08-23

<400> SEQUENCE: 11
```

| | | | | | |
|---|---|---|---|---|---|
| ggctcccggc | cagctgcgag | tcttggctcc | cggacttgtc | tcgtcgcgtc | ggagaaatcg        60 |
| ccccccagcg | ccgctctccc | gcccgggggt | cttggttccg | agctcgcgcg | gccgggagtc       120 |
| gcctcggtct | tccttggggc | gcgcgcagat | gtgagcgtgc | gagagttgtg | tagggganttt      180 |
| tgttccctcc | gaaactgaga | cccagggcgc | ccagtgggca | ccgtgccctt | gactctgtcc       240 |
| tttctgcagc | cgctggtccg | agctgtctgg | cctcagtttc | cctccgactt | ttctccgctc       300 |
| tgccagccct | cactgctgcc | cgtcattgtt | ctcgcagtta | gatggggggtg | ctttgtgacg      360 |
| gctgccaagt | tgggtgtgtg | tctctttatt | ccgttttca  | aacagaacaa | ggcctccaag       420 |
| gctgaccccca | gacaacccac | ccctcggac | cctaattcac | cttattgcac | tgatttttt        480 |
| tatcaagtcg | tattttattg | tacaggagcc | acgccctgat | ttcttaaagg | cgccttgcac       540 |
| tctggccatg | tgttatctct | gcagccggtg | tgcgggaggc | ctcttgtgag | ccagttgttt       600 |
| tcccgcctcc | accaccccc  | tcgaagattt | agggatgcca | gggggggaaga | aggtggctgg      660 |
| gggtggcagc | agcggtgcca | ctccaacgtc | cgctgcggcc | accgccccct | ctggggtcag       720 |
| gcgtttggag | accagcgaag | gaacctcagc | ccagagagat | gaggagccag | aagaggaagg       780 |
| ggaagaggac | ctgcgagacg | gaggcgtccc | cttctttgtc | aaccggggtg | ggctacctgt       840 |
| ggatgaggcc | acctgggaaa | ggatgtgaa  | acacgtggcc | aagatccacc | ccgatgagaa       900 |
| gaaggtggcg | caacggatcc | gtggggccac | agacctgccc | aagatcccca | taccgagtgt       960 |
| gcctacgttc | cagccgtcta | cacctgtccc | tgagcgcctg | gaagctgtgc | agcgctatat      1020 |
| cagagagctg | cagtacaatc | acacagggac | acagttcttt | gaaattaaga | agagcagacc      1080 |
| tctgacaggg | ctgatggacc | tggccaagga | aatgaccaaa | gaggccctgc | caatcaaatg       1140 |
| cctggaagcc | gtgatcctgg | gaatttacct | caccaacagc | atgcccaccc | tggagcgctt      1200 |
| ccccatcagc | ttcaagacct | acttctcagg | gaactacttc | cgccacatcg | tgctgggggt      1260 |
| gaacttcgcg | ggccgctacg | gtgcgctggg | catgagtcgg | cgcgaggacc | tgatgtacaa      1320 |
| gccgccgcc  | ttccgcacgc | tcagcgagct | cgtgctggac | ttcgaggccg | cctacggccg      1380 |
| ctgctggcac | gtgctcaaga | aggtgaagct | gggccagagc | gtgtcacacg | acccgcacag      1440 |
| cgtggagcag | atcgagtgga | agcactcggt | gctggacgtg | gagcgcctgg | gccgcgatga      1500 |
| cttccgcaag | gagctggagc | gccacgcccg | cgacatgcgg | ctcaagattg | gcaaagggac      1560 |

```
gggccctccc tctcccacca aggaccggaa gaaggatgtt tcttccccgc agcgggccca    1620
gtccagcccc caccgcagga acagccgcag tgaaagacgg ccctcgggtg acaagaagac    1680
ttccgagccc aaagccatgc cagaccttaa cgggtaccag atccgggtct gaggcggatg    1740
ccagcacccc aggccccacc cactcttggg ggccaggatc cacctgctgg aaccagcctt    1800
atgcatgggg aaggcggggc tggtgacaag gcagggcaag aggctgcagg aagagtgtgt    1860
tccagctcag cccccaagc tgctctcgct cccactgagc caagcccct aactttgggc      1920 ctagaggccg ttagtatttt atttggagtt tttaactcta caactgaagt ttaaggtatt    1980
tggggaaaac ttagtccaaa tggatctgct gatggtggga aggccagtgc ttaacaaatc    2040
catgtgtcat ggggccaggt gagggaaact gctggttctg ctggtgcctc tgcccctggc    2100
ttccctctgg gagttgggtg catcttatca gtgggaaatc tcccagcctt accaggcctg    2160 tgatggggg tggggtggg gtggagatgt ttctccagtt ctgcctgccc tggcagaatc      2220
ttgacccagg gaagggaag cagggtagga gtccttctga gaaaggtctg tgtagcccat     2280
taaccaggag cttggcacag gccacatctg ccccaagagc atgagctcgt ggctcaggag    2340
agccttcagg cccttgaggc ccccatgggc agtgctgtgt gggcagagga ggggtgatat    2400
gagagcgagc ccagggaagg acctctgggc aaaaagttcc caggccctaa ctgcgtctac    2460
ttgctcagtc ccagctctgc ctgttgctct agcccacagg ctcctgcgga gggtctgggc    2520
ttggcggagg acccagaatg gcactgaggc cagcatggct gtgggagttg agcaaaccct    2580
gggtgccagt ccaggagctg tggctggaca tggggtgatg gggcgggatg cttgggcctg    2640
ggtctctccg ccagcagtgc caggagccct tgctggggaa atcaagacca gactaggatg    2700
cttctgcccc aggcctgcct tccattcttt aacagcccat cttggcttgg ggttgcaatg    2760
atggctgggc cagtcacttg tggcagggca tcagggccct ggcagggaag aacctaggca    2820 cctgggttg tccccagcct gcccgtcagc atgagatacc cagtgggaaa gtgagaggat     2880
gcggagaggt tggcagagcc aggggtaggt tctggaggct caagcaacaa ggaggtgcag    2940
gtaaagggtg cagtgcagcc actgagggac agctgggaac tggggatgc aagtgagaaa     3000 gggatgtggg ggagagttca ggatcaggct gcttgaggag taatgggtta cctacagcag    3060
agacgagatg gctgtttgtc aggaggcggt agaaaggtag aaaggattca gattgtggaa    3120
gggtaaatgg atgagatgac cattaaggtt ttgtttact gagaggctgt aagtctgcca     3180
gggacagctg tcagtaaggc tgcagaaggg ctgggggct acacaaggaa gagcagaact     3240
agggttgtaa gctcaaatga cgagcaagcg gtgagaagga ggcctgaagg gctgtgtggg    3300
gactatggct acctgaagag ggcacaccct gttaaagggg ccacagctgc tcagctgttc    3360
ttacagtgcc ggccctgtgt tgccagattg tctgctttgt cagaggccag aattctgact    3420
ttttatgtga aataggattt ttaaatgctg gtgatcactt aaaaaaaact taaaaaccca    3480
atactggcaa aagaggatgc cagtctgcaa tccctgaagt agagagagct cgtgctgggg    3540
agaagtccac caagatgctt tgaggcgggc tgtagcaaag tcctgtttct cagagctggg    3600
ctgggctggg gtaggatcct tgcagctgag gaggaggaaa agccactgag tctcctccca    3660
gagcgggaca aaccagaggc cctttgcagt tgctgggtca ccagcggggg tggcgcatgg    3720
agtacagaca gtgtagctct tggcctgcca gggagacgga tggtgccttt gaagcaaaga    3780
ggaagggaag gcagaaccag ggatgccttt gctgatgaga gtgcctgtca gggaaggcgc    3840
cacaggctgg cagtcttcca aaccagcagc gcttgaccca gagccagatc cagcatggcc    3900
tggccagagg caccctggga ggccagctgg tcagtccctt gcctcccaa gttcccctg      3960
```

-continued

```
gggtcaatga gccctgggag gatgcctaac ctaactccag ccagactaat aggggcatgg    4020
tgacccttga ctcaccatcc catcccagct ttcaggagt ggggtagtg tggtctccat      4080 gttcctacta tgcctaagaa gagatggctc accttgggag gtgccaggct gaaactaggt    4140
cctttccggg tctggatgct gccgctcagg agcaggggcg tggcctcagc tgcctctggg    4200
agcttcccgg gaatgacagg gtttgagggg agtagatatg agagggagcc gctcctggtt    4260
ctggagtctt aggaggttcc aacttgcagg atcctttccc agagccctcc atggagaaaa    4320
cagcaaaatg aagcccttac ctgcttgctg tctgcaaggg agggagccga ccccagctg     4380 ataatccccc agcactcacc cttcctgagc tgaggcttcg gggctgtgga gaccagcaca    4440
ggacatagtg gtgcttttta aatttatttt taactgtttc tcatatgtag caacccctcc    4500 tccctcctg ggcatgttta cacaggctct gctctggggg ctggcctggc tgtgaggttt     4560
ctggggaggc agagaggcag ggactttggg gccttagtca ccatccatgg tatcacctca    4620
tctcacttcc tgtgagggac agggcctggc tgatgtgatc ccagctcccc ccagttcagg    4680
actgtctttc agctcctttg cccctggagg tgggggctgc tggctgagga ggggtcaagg    4740
tgagttcaag aaagctacct gtggaaaatg gaccaggttg ggggggtgat tgcaaagtct    4800
ccccaaagcc tggctcctca tgctcagtgc caggggcaga acactgggga gccaggtata    4860
gagagccttc ctgtcataac tgccagtcct cttcctccaa ggcctctgca tattctcatg    4920
ttcccctcac ccatcatgcc agccacccct atccctcttc tagcagggcc aagatgggga    4980
cagtagcagc cctctggact tgggatgtga tgataaagca agcctagggc cagggtttgg    5040
ggagcagaga gagccaagaa gttgaccacg tgtgatttcc agcccttccc actgggactt    5100
gacttcccag gtcaaggagt ccgtctcatt ctggctggtc gagtgaccag aggcctgtgt    5160
gaatgtgtgc acctgctttt cctgcctgga atgttttctg gctcagctgc agcaacatct    5220
gtgagcccag tgtctgccct gtgtccctgg gctcgctcca agtgcaggaa cgtacatgca    5280
gggcccaaca tgatgatggt gtgaagggca ggaaacagtc ctctgaagga gtggggaggt    5340
gggcagtctg cccccgccag gtaccatcgc ctcctgccag cttccttaga ccaggcaggg    5400
ctgccatggt gctagctgca agtccatcag tattgaccgt ctcgctccat cttggccctc    5460
cggagtccca agtttccttt tcatcaaatc tgacaagaga gaagaaacat gggtgtgctt    5520
ggcccacagg gcctggtggt gatggacctc cccgctccct caagctctgg atggctgcag    5580
tgttgtacta gactttgttc aggctgttct catctcagta ttgccccttc ctttcacttt    5640
cacacttcat ctcattcctg ttgtcacttt ccccgaaacg aataaagtct ccccagctcc    5700
tgctgtgtag gctgggcaga aaccacaaaa aaaaaaaaaa aaaaaaa                  5747
```

<210> SEQ ID NO 12
<211> LENGTH: 365
<212> TYPE: PRT
<213> ORGANISM: Homo sapiens
<300> PUBLICATION INFORMATION:
<308> DATABASE ACCESSION NUMBER: NCBI/NP_055724
<309> DATABASE ENTRY DATE: 2004-08-23

<400> SEQUENCE: 12

```
Met Pro Gly Gly Lys Lys Val Ala Gly Gly Ser Ser Gly Ala Thr
1               5                   10                  15

Pro Thr Ser Ala Ala Ala Thr Ala Pro Ser Gly Val Arg Arg Leu Glu
                20                  25                  30

Thr Ser Glu Gly Thr Ser Ala Gln Arg Asp Glu Glu Pro Glu Glu Glu
            35                  40                  45
```

```
Gly Glu Glu Asp Leu Arg Asp Gly Val Pro Phe Phe Val Asn Arg
 50                  55                  60
Gly Gly Leu Pro Val Asp Glu Ala Thr Trp Glu Arg Met Trp Lys His
 65                  70                  75                  80
Val Ala Lys Ile His Pro Asp Gly Glu Lys Val Ala Gln Arg Ile Arg
                 85                  90                  95
Gly Ala Thr Asp Leu Pro Lys Ile Pro Ile Pro Ser Val Pro Thr Phe
                100                 105                 110
Gln Pro Ser Thr Pro Val Pro Glu Arg Leu Glu Ala Val Gln Arg Tyr
            115                 120                 125
Ile Arg Glu Leu Gln Tyr Asn His Thr Gly Thr Gln Phe Phe Glu Ile
        130                 135                 140
Lys Lys Ser Arg Pro Leu Thr Gly Leu Met Asp Leu Ala Lys Glu Met
145                 150                 155                 160
Thr Lys Glu Ala Leu Pro Ile Lys Cys Leu Glu Ala Val Ile Leu Gly
                165                 170                 175
Ile Tyr Leu Thr Asn Ser Met Pro Thr Leu Glu Arg Phe Pro Ile Ser
                180                 185                 190
Phe Lys Thr Tyr Phe Ser Gly Asn Tyr Phe Arg His Ile Val Leu Gly
            195                 200                 205
Val Asn Phe Ala Gly Arg Tyr Gly Ala Leu Gly Met Ser Arg Arg Glu
        210                 215                 220
Asp Leu Met Tyr Lys Pro Pro Ala Phe Arg Thr Leu Ser Glu Leu Val
225                 230                 235                 240
Leu Asp Phe Glu Ala Ala Tyr Gly Arg Cys Trp His Val Leu Lys Lys
                245                 250                 255
Val Lys Leu Gly Gln Ser Val Ser His Asp Pro His Ser Val Glu Gln
                260                 265                 270
Ile Glu Trp Lys His Ser Val Leu Asp Val Glu Arg Leu Gly Arg Asp
            275                 280                 285
Asp Phe Arg Lys Glu Leu Glu Arg His Ala Arg Asp Met Arg Leu Lys
        290                 295                 300
Ile Gly Lys Gly Thr Gly Pro Pro Ser Pro Thr Lys Asp Arg Lys Lys
305                 310                 315                 320
Asp Val Ser Ser Pro Gln Arg Ala Gln Ser Ser Pro His Arg Arg Asn
                325                 330                 335
Ser Arg Ser Glu Arg Arg Pro Ser Gly Asp Lys Lys Thr Ser Glu Pro
            340                 345                 350
Lys Ala Met Pro Asp Leu Asn Gly Tyr Gln Ile Arg Val
        355                 360                 365

<210> SEQ ID NO 13
<211> LENGTH: 20
<212> TYPE: DNA
<213> ORGANISM: Artificial sequence
<220> FEATURE:
<223> OTHER INFORMATION: Primer of Vasohibin-2

<400> SEQUENCE: 13
gcagccatga agccaaccgt                                              20

<210> SEQ ID NO 14
<211> LENGTH: 20
<212> TYPE: DNA
<213> ORGANISM: Artificial sequence
```

```
-continued

<220> FEATURE:
<223> OTHER INFORMATION: primer of Vasohibin-2

<400> SEQUENCE: 14
ctcttgctgg ccggtatggg                                                          20
```